(12) United States Patent
McIntosh et al.

(10) Patent No.: US 9,452,022 B2
(45) Date of Patent: *Sep. 27, 2016

(54) DISPOSABLE WAND AND SENSOR FOR ORTHOPEDIC ALIGNMENT

(75) Inventors: Jason McIntosh, Sugar Hill, GA (US); Marc Boillot, Plantation, FL (US)

(73) Assignee: ORTHOSENSOR INC, Dania Beach, FL (US)

(\*) Notice: Subject to any disclaimer, the term of this patent is extended or adjusted under 35 U.S.C. 154(b) by 72 days.

This patent is subject to a terminal disclaimer.

(21) Appl. No.: 12/982,944

(22) Filed: Dec. 31, 2010

(65) Prior Publication Data

US 2011/0160572 A1    Jun. 30, 2011

Related U.S. Application Data

(60) Provisional application No. 61/291,725, filed on Dec. 31, 2009.

(51) Int. Cl.
| | |
|---|---|
| *A61B 17/58* | (2006.01) |
| *A61B 17/60* | (2006.01) |
| *A61F 2/00* | (2006.01) |
| *A61B 19/00* | (2006.01) |
| *A61B 8/00* | (2006.01) |

(52) U.S. Cl.
CPC ............ *A61B 19/5244* (2013.01); *A61B 8/565* (2013.01); *A61B 8/58* (2013.01); *A61B 34/20* (2016.02); *A61B 8/56* (2013.01); *A61B 2034/2048* (2016.02); *A61B 2034/2063* (2016.02)

(58) Field of Classification Search
CPC ............... A61B 8/15; A61B 19/5244; A61B 2019/5248; A61B 2019/5276; A61B 8/154; A61B 8/155; A61B 8/157; A61B 8/158
USPC .............. 606/86 R, 87–90, 91, 96, 102, 105; 600/424–429, 448
See application file for complete search history.

(56) References Cited

U.S. PATENT DOCUMENTS

| | | | |
|---|---|---|---|
| 5,274,363 A | 12/1993 | Koved | |
| 5,285,677 A * | 2/1994 | Oehler | ..................... 73/24.01 |
| 6,090,114 A | 7/2000 | Matsuno et al. | |
| 6,130,663 A | 10/2000 | Null | |
| 6,137,427 A | 10/2000 | Binstead | |
| 6,313,825 B1 | 11/2001 | Gilbert | |
| 6,490,467 B1 | 12/2002 | Bucholz et al. | |
| 6,508,403 B2 * | 1/2003 | Arsenault et al. | ............ 235/454 |
| 6,546,277 B1 | 4/2003 | Franck et al. | |
| 6,859,661 B2 * | 2/2005 | Tuke | ............................ 600/424 |
| 6,925,339 B2 | 8/2005 | Grimm et al. | |
| 6,937,227 B2 | 8/2005 | Qamhiyah | |
| 7,078,911 B2 | 7/2006 | Cehelnik | |
| 7,081,884 B2 | 7/2006 | Kong | |
| 7,092,109 B2 | 8/2006 | Satoh et al. | |
| 7,130,754 B2 | 10/2006 | Satoh | |
| 7,139,418 B2 | 11/2006 | Abovitz et al. | |
| 7,309,339 B2 | 12/2007 | Cusick | |
| 7,392,076 B2 | 6/2008 | Moctezuma de La Barrera | |
| 7,395,181 B2 | 7/2008 | Foxlin | |

(Continued)

*Primary Examiner* — Kevin T Truong
*Assistant Examiner* — Si Ming Ku

(57) ABSTRACT

A disposable tool suitable for use in orthopedic alignment that registers points of interest on a first and second bone and transmits location data related to the points of interest to the sensor to assess orthopedic alignment with the points of interest. A display can report and visually display alignment information in real-time.

19 Claims, 16 Drawing Sheets

(56) References Cited

U.S. PATENT DOCUMENTS

| | | |
|---|---|---|
| 7,477,926 B2 * | 1/2009 | McCombs .................... 600/407 |
| 7,559,931 B2 | 7/2009 | Stone |
| 7,604,645 B2 | 10/2009 | Barzell et al. |
| 7,636,595 B2 | 12/2009 | Marquart |
| 7,657,298 B2 | 2/2010 | Moctezuma de la Barrera et al. |
| 7,660,623 B2 | 2/2010 | Hunter et al. |
| 7,681,448 B1 | 3/2010 | Preston et al. |
| 7,685,861 B2 | 3/2010 | Lynch et al. |
| 7,689,032 B2 | 3/2010 | Strassenburg-Kleciak |
| 7,771,436 B2 | 8/2010 | Moctezuma et al. |
| 7,824,328 B2 | 11/2010 | Gattani et al. |
| 8,046,050 B2 | 10/2011 | Govari et al. |
| 8,057,479 B2 | 11/2011 | Stone |
| 8,068,648 B2 | 11/2011 | DiSilvestro et al. |
| 8,267,866 B2 * | 9/2012 | Levin ........................... 600/438 |
| 2001/0011175 A1 | 8/2001 | Hunter et al. |
| 2003/0004518 A1 * | 1/2003 | Perren et al. ................. 606/102 |
| 2003/0132913 A1 | 7/2003 | Issinski |
| 2004/0024309 A1 | 2/2004 | Ferre et al. |
| 2004/0215079 A1 * | 10/2004 | Omura et al. ................ 600/459 |
| 2004/0236424 A1 | 11/2004 | Berez et al. |
| 2004/0254584 A1 | 12/2004 | Sarin et al. |
| 2006/0030771 A1 * | 2/2006 | Levine et al. ................ 600/424 |
| 2006/0092022 A1 | 5/2006 | Cehelnik |
| 2006/0132120 A1 * | 6/2006 | Luber et al. ............. 324/207.16 |
| 2006/0161051 A1 * | 7/2006 | Terrill-Grisoni et al. .... 600/300 |
| 2006/0161871 A1 | 7/2006 | Hotelling |
| 2006/0164241 A1 | 7/2006 | Makela |
| 2006/0224429 A1 | 10/2006 | Mathew |
| 2006/0235420 A1 | 10/2006 | Irving |
| 2006/0256090 A1 | 11/2006 | Huppi |
| 2007/0127039 A1 | 6/2007 | Njolstad |
| 2007/0175489 A1 | 8/2007 | Moctezuma et al. |
| 2007/0288194 A1 * | 12/2007 | Boillot .......................... 702/150 |
| 2008/0269599 A1 | 10/2008 | Csavoy et al. |
| 2009/0318836 A1 | 12/2009 | Stone et al. |
| 2010/0063508 A1 | 3/2010 | Borja et al. |
| 2010/0069911 A1 | 3/2010 | Borja et al. |
| 2010/0076505 A1 * | 3/2010 | Borja ........................ 606/86 R |
| 2010/0137869 A1 | 6/2010 | Borja et al. |
| 2010/0160771 A1 | 6/2010 | Gielen et al. |
| 2010/0210939 A1 | 8/2010 | Hartmann et al. |
| 2012/0232834 A1 | 9/2012 | Boillot |
| 2012/0253200 A1 | 10/2012 | Boctor |
| 2012/0316486 A1 | 12/2012 | Cheung et al. |

* cited by examiner

GUI IDENTIFIES DIRECTION AND DISTANCE OF THE SENSOR CONFIGURATION TO SHOW TRACKING PERFORMANCE OF ONE SENSOR (S1) AS IT IS MOVED IN 3D SPACE

GUI VISUALLY IDENTIFIES LOCATION OF FEMUR HEAD FROM ROTATIONAL MOVEMENT OF THE FEMUR

GUI SHOWS 3D MAPPING OF LEG MOVEMENT IN PHYSICAL SPACE TO THE DISPLAY AND REPORTS RANGE OF TION AND ALIGNMENT

DISPOSABLE WAND AND SENSOR FOR ORTHOPEDIC ALIGNMENT

CROSS-REFERENCE TO RELATED APPLICATIONS

This application claims the priority benefit of U.S. provisional patent application No. 61/291,725 filed Dec. 31, 2009, the disclosure of which is incorporated herein by reference in its entirety. This application also claims the benefit of U.S. patent application Ser. No. 12/901,094 filed Oct. 8, 2010, the disclosure of which is incorporated herein by reference in its entirety.

FIELD OF THE DISCLOSURE

The present disclosure relates generally to orthopedic medical devices and more specifically to portable assisted navigation surgical tools.

BACKGROUND

A total knee replacement is a surgical procedure whereby the diseased knee joint is replaced with artificial material and prosthetic components. The knee is a hinge, which provides motion at the point where the femur meets the tibia. During a total knee replacement, the distal end of the femur bone is removed and replaced with a femoral component. The proximal end of the tibia is also removed and replaced with a tibial component. Depending on the condition of the kneecap portion of the knee joint, a button may also be added under the kneecap surface.

During total knee replacement surgery it is imperative that the bone cuts on the femur and tibia are made to result in proper alignment. The alignment ensures proper balance and straightness of the leg. The bone cuts can be made with use of physical guides and jigs, and more recently, with significant success, by way of highly accurate computer assisted systems.

A need however can arise for low cost portable and disposable surgical tools to provide assisted alignment in orthopedic surgical procedures.

DETAILED DESCRIPTION

Embodiments in accordance with the present disclosure provide an apparatus and method of assisted guidance navigation for surgical assisted alignment.

In one embodiment, a disposable tool suitable for use in orthopedic surgery comprises a primary sensor and a wand to register points of interest on a first and second bone. The wand can be attached to a cutting jig for reporting an orientation with respect to anatomical alignment. The primary sensor and wand use ultrasonic sensing and tracking to determine their relative location to one another including the cutting jig when attached; both of which are wireless. Based on the registered points of interest, the primary sensor can then assess and report parameters related to the orientation of the cutting jig for establishing cutting angles to align the first and second bone. The primary sensor can communicate with a remote (optional) communication device via a wireless connection to report and visually display alignment information in real-time.

Ultrasonic tracking and navigation can provide certain benefits over conventional available Computer Assisted Surgery (CAS) systems. Commercial CAS systems are based on different navigation principles (e.g., active or passive optical or electromagnetic) where precise intra-operative orientation is provided by high-resolution imaging techniques (e.g., computed tomography (CT), magnetic resonance imaging (MRI)). These systems generally require the placement of fiducial markers, CT or MRI imaging, data transfer to the operating room (OR), and identification and registration of the fiducials. They are also sensitive to deviations in light intensity, contrast, and reflections. When performing these preparatory and practice steps, each platform has individual needs and a number of potential deficiencies influencing the accuracy of the system.

CAS platforms generally consist of three main parts: a mobile workstation, a position interface (e.g., camera system) and an instrument pointer. The mobile workstation is the hub between the position interface and the instrument pointer. It is generally positioned away from the surgical area yet close enough to track the instrument pointer. Although it requires minimal space in the operating room and is sufficiently mobile, it is generally a capital expense that is maintained on-site. The instruments must be sterilized with each use and the sophisticated optical components are custom made.

The ultrasonic disposable tool in contrast comprises a primary sensor and wand that are both wireless and can communicate directly with one another; no mobile workstation is required between the two. Constructed with low-cost ultrasonic transducers and electronic components it is suitable for up to 2-4 hours of use and can thereafter be disposed, thereby incurring less hospital support and overhead.

Figure 1A:
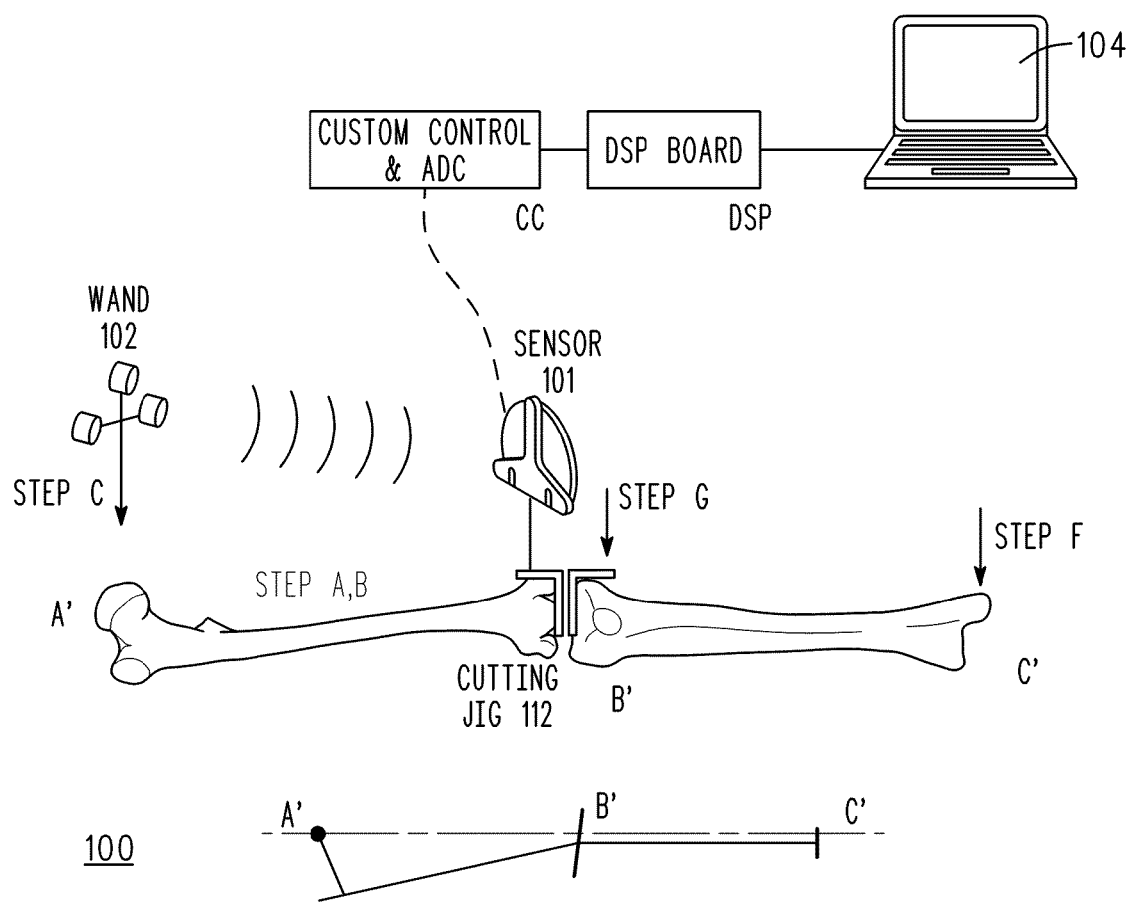
FIG. 1A depicts an exemplary illustration of a portable alignment system in accordance with one embodiment.

FIG. 1A depicts an exemplary embodiment of a portable wireless alignment system 100 suitable for use as an alignment tool in orthopedic surgery. The system 100 includes a primary sensor 101, a wand 102, and a portable communication device 104; all of which can be wireless. In one embodiment, the sensor 101 and wand 102 each have at least two ultrasonic transducers to support the identification of a location in three-dimensional space. One example of providing sensory feedback in a navigated workflow with the sensorized tools is disclosed in U.S. patent application Ser. No. 12/900,662 entitled "Navigation Device Providing Sensory Feedback" filed Oct. 8, 2010; the entire contents of which are hereby incorporated by reference.

As shown, sensor 101 and wand 102 each have three ultrasonic transducers. In one, embodiment, the wand 102 transmits ultrasonic signals and sensor 101 detects ultrasonic signals. In a surgical setting, system 100 measures time of flight and differential time of flight of the transmitted ultrasonic signals for location determination within a surgical field of an operating room. A trigger system is provided on system 100 that initiates the time of flight and differential time of flight measurements. In the example, the trigger system is an infrared or optical system coupled between wand 102 and sensor 101. For example, an optical transducer on wand 102 sends a pulsed optical signal that initiates a measurement. The sensor 101 has an optical transducer for detecting the pulsed signal. A measurement sequence is initiated when the pulsed optical signal is received. In general, the optical signal is received almost instantaneously when compared to a simultaneously transmitted ultrasonic signal. The primary sensor 101 and wand 102 are low cost components that can be disposed after surgery. The wand 102 is used to register points of interest with the primary sensor 101. The points of interest can be on the bone or on cutting jigs 112 used during surgery. The system 100 reports alignment of the bones or cutting jigs 112 by way of the wand 102 and the primary sensor 101. The system 100 can assist the surgeon in establishing alignment of the cutting jigs 112 and bones and evaluating surgical process of alignment during and after surgery. The system 100 further includes at least one mount within the surgical field. The mount retains and holds the wand in a predetermined location during the surgery after points of interest have been registered. In one embodiment, the sensor 101, wand 102, and the mount are maintained within the surgical field.

As one example, alignment is achieved when the points of the femur head (A'), patella (B') and ankle (C') are positioned in a straight line. As will be explained ahead in more detail, the portable wireless alignment system 100 intra-operatively assesses alignment of the femur and tibia bones during knee surgery. Certain aspects of alignment preparation can be performed prior to surgery as will be discussed ahead. It can also transmit this information to associated wireless devices (e.g., laptop, cell phone, net book) and upload the information to a server on a network for example one connected to electronic medical or health care records. The system 100 assesses and reports in real-time the position of these points, or other registered points, by way of a graphical user interface on the communication device 104. In one embodiment, communication device 104 is a laptop computer. The communication device 104 can be outside the sterile field but positioned such that a surgeon and surgical team can view the display while utilizing wireless alignment system 100. It provides visual and auditory feedback related to alignment, such as audible acknowledgements, haptic sensation (e.g., vibration, temperature), and graphical feedback (e.g., color-coded line data).

Although shown as a coupled system, the wand 102 and the sensor 101 can operate independently of the communication device 104. The custom control board (CC) and the DSP are integrated and scaled down onto the sensor 101 for local communication (e.g., close distance, paired) and processing. In this configuration the wand 102 and the sensor 101 alone can assess and report alignment. As will be discussed ahead, the sensor 101 includes a user interface that visually and audibly reports alignment status. Afterward, the sensor 101 can be communicatively coupled to the communication device 104 or server to download alignment information or other captured data.

Figure 1B:
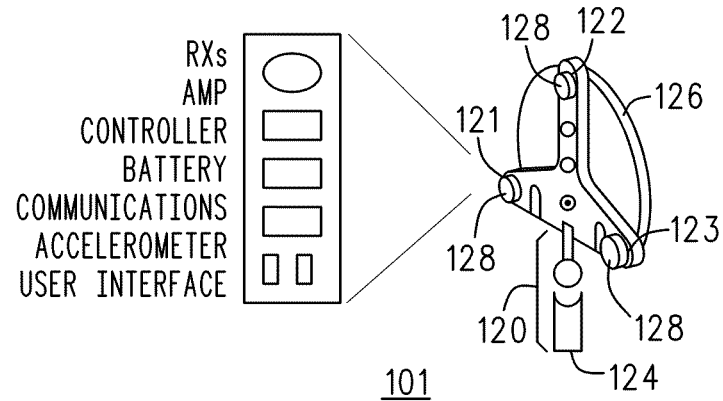
FIG. 1B depicts a wireless sensor for assisted alignment in accordance with one embodiment.

FIG. 1B depicts an exemplary embodiment of the primary sensor 101. The sensor 101 can comprise two or more ultrasonic transducers 121-123 for three-dimensional sensing. In one arrangement, each side of sensor 101 can include a set of transducers 121-123. In the illustration, the transducers 121-123 are mounted at predetermined positions or locations on a support structure. In one embodiment, the support structure is a printed circuit board (PCB) 126. The predetermined positions of transducers 121-123 are spaced to support the measurement of time of flight and differential time of flight signals by each sensor for location identification. In the example, the ultrasonic tranducers 121-123 are mounted planar to the surface of the PCB 126 and co-planar to one another. The ultrasonic transducers can be MEMS microphones, ultrasonic receivers, ultrasonic transmitters or combination thereof. As one example, each ultrasonic transducer can perform separate transmit and receive functions. One example of an ultrasonic sensor is disclosed in U.S. patent application Ser. No. 11/683,410 entitled "Method and Device for Three-Dimensional Sensing" filed Mar. 7, 2007 the entire contents of which are hereby incorporated by reference.

As described herein, additional transducer placed on a second side of PCB 126 would be performed in a similar manner. The transducers 121-123 can be covered with a material 128 or screen that is transmissive to ultrasonic frequencies. The material 128 protects and prevents liquid or solid matter generated during a surgery from affecting or modifying the performance of transducers 121-123.

The sensor 101 can include an amplifier, a battery or power source, a communications module (e.g., Radio Frequency modulator), an accelerometer, and a controller. In one embodiment, the components are mounted to PCB 126 and operatively coupled to form a circuit with transducers 121-123 to support three-dimensional sensing. The amplifier enhances the signal to noise of transmitted or received signals. The communications module can include components (e.g., synchronous clocks, infrared, optical/acoustic pulse) for local signaling (sensor 101 to wand 102) or network components (e.g., Bluetooth, ZigBee, Wi-Fi, GPSK, FSK) for wireless communications with the communication device 104 (sensor 101 and wand 102 to a laptop 104 or other equipment) for sending alignment data or information thereto. An optical or infrared transducer can be mounted on PCB 126. In one embodiment, the optical or infrared transducer receives a trigger signal for initiating a measurement as will be disclosed in more detail hereinbelow. The trigger signal is substantially faster than an ultrasonic signal. In the example, the trigger signal is launched from wand 102. The accelerometer identifies axial tilt (e.g., 3/6 axis) during motion and while stationary. The controller is coupled to the transducers 121-123 and the accelerometer to receive data provided therefrom to determine a location of an object in three-dimensional space within a surgical field. The controller can include a counter, a clock, and other analog or digital logic for controlling transmit and receive synchronization and sequencing of the sensor signals, accelerometer information, and other component data or status. The battery powers the respective circuit logic and components.

The controller can utilize computing technologies such as a microprocessor (μP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips, for example, specific to a core signal-processing algorithm. The controller can be an embedded platform running one or more modules of an operating system (OS). In one arrangement, the storage memory may store one or more sets of instructions (e.g., software) embodying any one or more of the methodologies or functions described herein. In the example, the controller is operatively coupled to an interface of sensor 101. The user interface alone or with laptop 104 can be used to visually, haptically, or audibly report a status.

The sensor 101 includes a mounting structure 120 for coupling to bone or a surgical cutting jig. As one example, the mechanism can be a magnetic assembly with a fixed insert (e.g., square post head) to permit temporary detachment. The mounting structure 120 positions can position sensor 101 in a reference position. In the illustration, sensor 101 is coupled to the distal end of the femur. As another example, it can be a magnetic ball and joint socket with latched increments. In one embodiment, the mounting structure 120 comprises a rod having first and second threaded ends. One threaded end couples to sensor 101 the remaining threaded end couples to a bone, cutting block, jig or other structure for supporting the device. A taper threaded region would be used to screw the mounting structure 120 into bone similar to an orthopedic screw. It is not limited to the embodiments disclosed herein and others are attachment methods are contemplated.

Figure 1C:
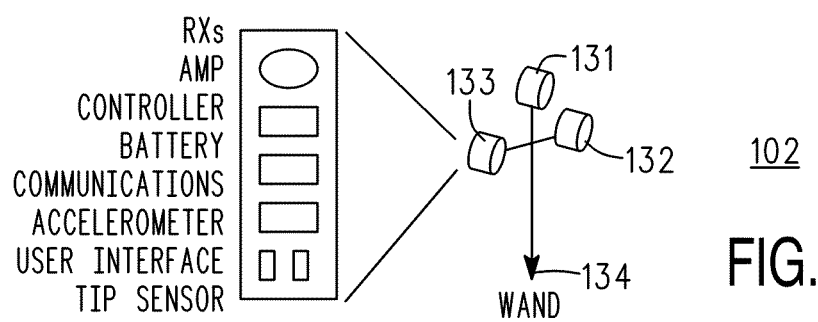
FIG. 1C depicts a wireless wand for assisted alignment in accordance with one embodiment.

FIG. 1C depicts an exemplary embodiment of the wand 102. The wand 102 can include two or more transducers 131-133 for three-dimensional position detection and sensing. In the illustration, the transducers 131-133 are mounted at predetermined positions or locations on wand 102. In one embodiment, the transducers are mounted on a printed circuit board. The printed circuit board is placed within an enclosure that allows wand 102 to be held in a hand. The wand 102 form factor will be described in more detail hereinbelow. The predetermined positions of transducers 131-133 are spaced to support the measurement of time of flight and differential time of flight signals by each transducer for location identification. In the example, the ultrasonic transducers 121-123 are mounted planar to the surface of the PCB 126 and co-planar to one another. The ultrasonic transducers can be MEMS microphones, ultrasonic receivers, ultrasonic transmitters or combination thereof.

A tip 134 of the wand can be used to identify points of interest on the muscular-skeletal system, bone, or cutting jig 112. The ultrasonic transducers can be MEMS microphones, ultrasonic receivers, ultrasonic transmitters, or combination thereof. The ultrasonic transducers can perform separate transmit and receive operations. The wand 102 can include an attachment mechanism for coupling to bone or a surgical cutting jig. One example of an ultrasonic sensing device is disclosed in U.S. patent application Ser. No. 11/683,416 filed Mar. 7, 2007 the entire contents of which are hereby incorporated by reference. It can be held in hand, to identify via the wand tip, points of interest, or coupled to an object to remain stationary. It can attach via a clip, clamp, magnetic base, slot, insert or other mechanism to a receiving object (e.g., operating room overhead lights, operating room table, monitor stands, etc.)

The wand 102 can include an amplifier, a battery or power source, a communications module (e.g., Radio Frequency modulator), an accelerometer, and a controller. In one embodiment, the components are operatively coupled to form a circuit with transducers 121-123 on the printed circuit board to support three-dimensional sensing. The amplifier enhances the signal to noise of transmitted or received signals. The communications module can include components (e.g., synchronous clocks, infrared, optical/acoustic pulse) for local signaling (sensor 101 to wand 102) or network components (e.g., Bluetooth, ZigBee, Wi-FI, GPSK, FSK) for wireless communications with the communication device 104 (sensor 101 and wand 102 to a laptop 104 or other equipment) for sending alignment data or information thereto. An optical or infrared transducer can be mounted on the printed circuit board or housing. In one embodiment, the optical or infrared transducer sends the trigger signal for initiating a measurement as will be disclosed in more detail hereinbelow. The accelerometer identifies 3 and 6 axis tilt during motion and while stationary. The controller, like the sensor 101 controller, can include a counter, a clock, or other analog or digital logic for controlling transmit and receive synchronization and sequencing of the sensor signals, accelerometer information, and other component data or status. The battery powers the respective circuit logic and components. The controller is coupled to the transducers 131-133 and the accelerometer to support identification of the location of an object in three-dimensional space.

The wand 102 can include a touch sensitive tip 104 that registers points responsive to a physical action, for example, touching the wand tip to a bone or jig. The tip 104 extends from the wand housing. The touch sensitive tip 104 can comprise a mechanical accelerometer or actuated spring assembly. In another arrangement, it includes a capacitive touch tip or electrostatic assembly. The wand 102 and sensor 101 may each further include a haptic module and a user interface. As an example, the haptic module may change (increase/decrease) vibration to signal improper or proper alignment status. It may include a temperature module to change to warm or cold responsive to operational status. The user interface can permit handheld operation and use (e.g., on/off/reset button) and provide visual feedback. As an example, one or more LED lights can show alignment and direction (left/right/up/down). The sensor 101 and the wand 102 can include material covering the transducers that are transparent to sound (e.g., ultrasound) and light (e.g., infrared) yet impervious to biological material such as water, blood or tissue. As an example, a clear plastic membrane can be stretched taught to vibrate under resonance with a transmitted frequency and provide a hermetic seal. The battery supply of the wand 102 and sensor 101 can be charged via wireless energy charging (e.g., magnetic induction coils and super capacitors).

The wand 102 can also be mounted or have a mount. In one embodiment, the wand 102 can include a mount to attach to a bone, cutting block, or jig. The mount can comprise a rod or fastener on or extending from the housing of wand 102 that can screw into or attach to a structure. A mount can comprise a stand that retains and places wand 102 in a fixed position. For example, a hanger can extend from a lighting system or ceiling of the operating room within the sterile field. The wand 102 can be placed on the hanger such that it remains in line of sight to sensor 101 during the measurement and alignment process. Alternatively, a stand or mount for wand 102 can be placed in the line of sight of sensor 101. The stand or mount retains wand 102 and can be fastened to a structure maintain a fixed position.

Figure 1D:
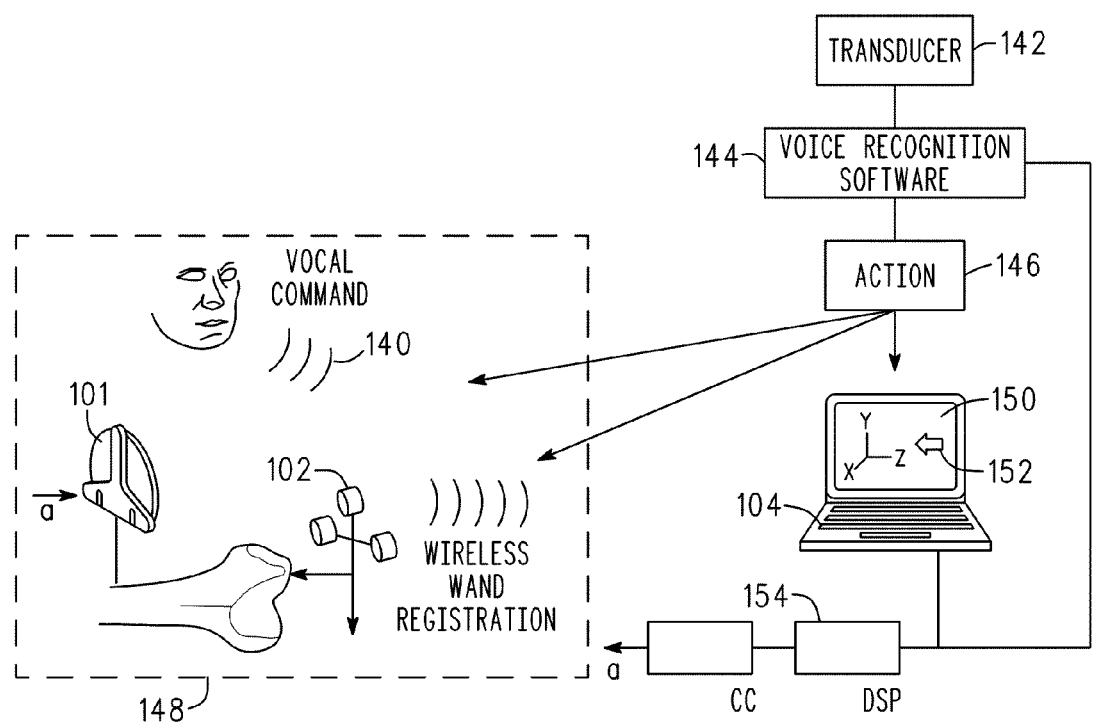
FIG. 1D depicts a diagram for wireless wand registration in accordance with one embodiment.

FIG. 1D depicts an exemplary diagram of wireless wand to register points of interest with the system 100 (e.g., communication device 104). During registration, the wand tip is touched to points of interest, for example, the distal femur center, to register the location with the sensor 101. The communication device 104 can visually show the movement of the wand 102 in 3D with respect to the sensor 101. The wand 102 and the sensor 101 can communicate via a local communications protocol (e.g. optical/ultrasonic pulsing) apart from the network communication (e.g., Bluetooth, Wi-Fi) between the sensor 101 and the communication device 104. In a master-slave configuration, the wand 102 serves as the slave to inform the sensor 101 of the points of interest, and the sensor 101 serves as the master for communication of the alignment information to the communication device 104.

In one embodiment, the wand 102 and sensor 101 communicate location information by way of ultrasonic pulsing and optical sequencing. The wand 102 emits high frequency sound pulses (e.g., 40-120 KHz) transmitted by each of the respective transmitters that arrive at the receivers of the sensor 101 at different times. The timing information between each of the received pulses and the time length of sound travel can be used to determine the location of the wand 102 relative to the sensor 101. Three sensors alone with this timing information can be used to establish three-dimensional coordinates of the wand 102. Sampling intervals on the order of 160 to 200 samples (16-bit) per second per transmitter are sufficient for real-time analysis and display. In another arrangement, only two sensors need be used on the wand to achieve a narrower physical profile for three-dimensional location and positioning based on spherical propagation characteristics of sound waves.

An example of voice recognition in an operating room or surgical environment is disclosed hereinbelow. The exemplary embodiment utilizes system 100 for alignment. A surgical field 148 is a region within the operating room where the patient resides and where the surgery is performed. The surgical field 148 is a sterile region that minimizes patient exposure when opened during surgery. One or more devices are used by the surgeon within the surgical field 148. In general, the devices are active devices having at least one sensor for performing a function or measuring a parameter. The active devices will further have communication circuitry to couple to an interface within the device or external for providing information or data.

An orthopedic surgical procedure is used as an example of applying voice recognition. As shown, sensor 101 and wand 102 are devices used by the surgeon to align two or more bones of the muscular-skeletal system. More specifically, the sensor 101 and wand 102 comprise an ultrasonic alignment system that is coupled to the patient within the surgical field. The devices can further include a prosthetic component having at least one sensor for measuring a parameter. For example, the prosthetic component can be an insert for measuring a parameter such as a force, pressure, or load applied to an articular surface by the muscular-skeletal system. The system 100 further includes the portable communication device 104. In one embodiment, the communication device 104 is a laptop computer having a display 150 with a GUI 152. The communication device 104 is wirelessly coupled to the devices within the surgical field 148 for receiving data from the sensors and displaying the information on display 150. The display 150 can be outside of the surgical field 148 but in view of the personnel in the surgical field 148. In the alignment example, the display 150 shows patient alignment and the measured parameter from the sensor in real-time. The measured parameter can be a load magnitude and position of load on the articular surface of the insert. The GUI 152 displays the quantitative data in a manner where the surgeon can consume alignment and the force, pressure, or load information simultaneously to rapidly apply the data to the joint installation.

A transducer 142 is within the operating room for receiving audio signals such as a vocal command. A digital signal processor 154 is coupled to the transducer 142 and other components of system 100 such as wand 102, sensor 101, display 150, the insert, and communication device 104. The audio signals received by transducer can be converted to a digital format for processing by the digital signal processor 154. Alternatively, the digital signal processor 154 can reside in portable communication device 104, sensor 101, or wand 102. In one embodiment, a vocal command produces an operative change or action 146 in the coupled system between the one or more devices or the display 150 in the operating room. For example, a voice command to "measure loading" can initiate the insert to take the action 146 to measure the load on the articular surface and display the position and magnitude of the load on the display 150. Similarly, a voice command such as "magnify" could result in an action 146 to increase the size of figures on the display 150. It should be noted that these are merely examples, many different types of voice commands would be useful in surgical environment, which would vary depending on the application.

The digital signal processor 154 is coupled to voice recognition software 144. The voice recognition software 144 can assess audio signals received from transducer 142. The voice recognition software 144 can deliver the audio to an application specific software program looking for specific words or phrases. As mentioned previously, the specific words or phrases can be directed to the application or procedure. In one embodiment, the voice recognition software 144 or other program identifies one or more words corresponding to an action and provides a query to the identified words. The query can be a visual or auditory queue that requires a response. The query is a failsafe that ensures that the action being taken is the one that was requested via the vocal command. The visual or auditory queue can be a restatement of the action as identified by voice recognition software 144. For example, a vocal response such as "yes" or "no" could be provided by the person who initiated the vocal command. The response provided to the query will result in the action being taken or the action terminated. In at least one exemplary embodiment, one or more of the active devices in the surgical field are disposable such that they are for a single use and disposed of after the surgery.

A method of improving operating room efficiency is provided in accordance with an exemplary embodiment. The steps disclosed herein can be performed in any order or combination. An operating room in a hospital or clinic is a clean room environment that limits and prevents exposure to organisms or materials that could be harmful to a patient during a surgical procedure. A surgical procedure is a very labor-intensive process that currently utilizes a large number of personnel. Moreover, the surgical procedure is performed within a surgical field of the operating room. The surgical field is a clean area where the patient, surgical personnel, and some equipment reside. Typically, movement of people, components, or material into and out of the surgical field is limited or restricted after the procedure has started.

A surgeon has to perform many physical tasks during surgery. Often, the surgeon is using both hands while concurrently directing other personnel during the procedure. The field of view or the direct view of the surgery is often not sufficient for the surgeon. Moreover, there are many tools being introduced that include electronic or electromechanical devices to provide data. A display can be used to provide data from measurement devices as well as view of the surgery. The display can also sequence through the steps of a surgical procedure as disclosed herein. In general, the display allows at a single glance a combination of information, data, and the surgery.

In the disclosed method, information related to a surgical procedure is displayed on a display in the operating room in a first step. Examples of information can be measured data, steps of a procedure, visual aids, or live video of the procedure. The information is presented in a GUI that enhances the efficiency and accuracy in which the procedure can be performed. In a second step, a command is vocalized to initiate an action. The action can be related to the display, devices taking measurements, or the procedure. Initiating the action results in a change to the device in which the action is directed. A transducer within the operating room receives the audio signal. The audio signal can be converted to a digital signal and further processed to enhance recognition. In one embodiment, the audio signal is processed by a digital signal processor (DSP) running voice recognition software. In a third step, the command is identified using the voice recognition software. For example, an action could be to select a page on the display, change an order of the images, zoom-in, zoom-out, to name but a few of the commands that would aid the surgeon while performing the surgery. Similarly, actions such as enable, disable, measure, and calibrate can control active devices used in the procedure. Although simple actions are provided as examples more sophisticated operations requiring more complex phrasing and software interpretation can be implemented.

Typically, voice command actions are used in a manner to maintain patient safety. In one embodiment, recognized words or phrases are not implemented directly. In a fourth step, a query is provided to the identified command. For example, the query can be visual, audible, or both. On query would be to show the identified action on the display or recite it audibly. In a fifth step, a response to the query is provided to initiate or terminate the action. For example, an audible response such as yes or no could be provided to answer the query. A "yes" response to the query would be received and identified by the voice recognition software. The affirmative response would send a signal to the appropriate device to initiate the action. Conversely, a "no" response received and identified by the voice recognition software could terminate the action. Further measures could be taken to ensure a correct response such as voice identification of the person initiating the action to prevent other audio input from triggering the action.

In a sixth step, one or more sensors are coupled to the patient. The one or more sensors measure a parameter corresponding to the surgery. Measurements such as pH, temperature, viscosity, electrical activity, load, density, pressure, force, distance, and alignment are examples of parameters that can be monitored during surgery. In a seventh step, the quantitative measurements from the one or more sensors are displayed in real-time on the display. As mentioned previously, the data can be provided in a format that aids the surgeon during the procedure. For example, bone alignment can be shown with bones being displayed on the display in relation to one another as the surgeon sees on the operating table. The bone and bone angles would change on the display in real-time as they are moved.

The steps of the procedure can be supported on the display. In an eighth step, the steps of the surgical procedure can be provided in sequence on the display. The measured parameters corresponding to the patient or the surgery can be provided on the display that supports the step of the procedure being performed. During the step, at least one voice command is initiated to generate an action related to the display or sensors. An example would be to register a point or location on the patient or turning to the next step in the procedure after the prior step was completed.

In a ninth step, adjustments are made during the surgical procedure that change the readings measured by the one or more sensors. The sensors report in real-time which is displayed on the display. The surgeon can benefit from seeing changes in quantitative data as modifications are being made. Furthermore, the surgeon can make fine adjustments to a specific parameter range while viewing the display or interfaces on the measurement devices. In a tenth step, the measurements can be recorded. In one embodiment, the surgeon can determine by voice command when data or a measurement is stored. In an eleventh step, the one or more sensors are disposed of after the surgical procedure. In the example, sensors are in contact with the patient. The devices having the sensors are designed for a single use and are disposed of along with any biological matter.

Figure 1E:
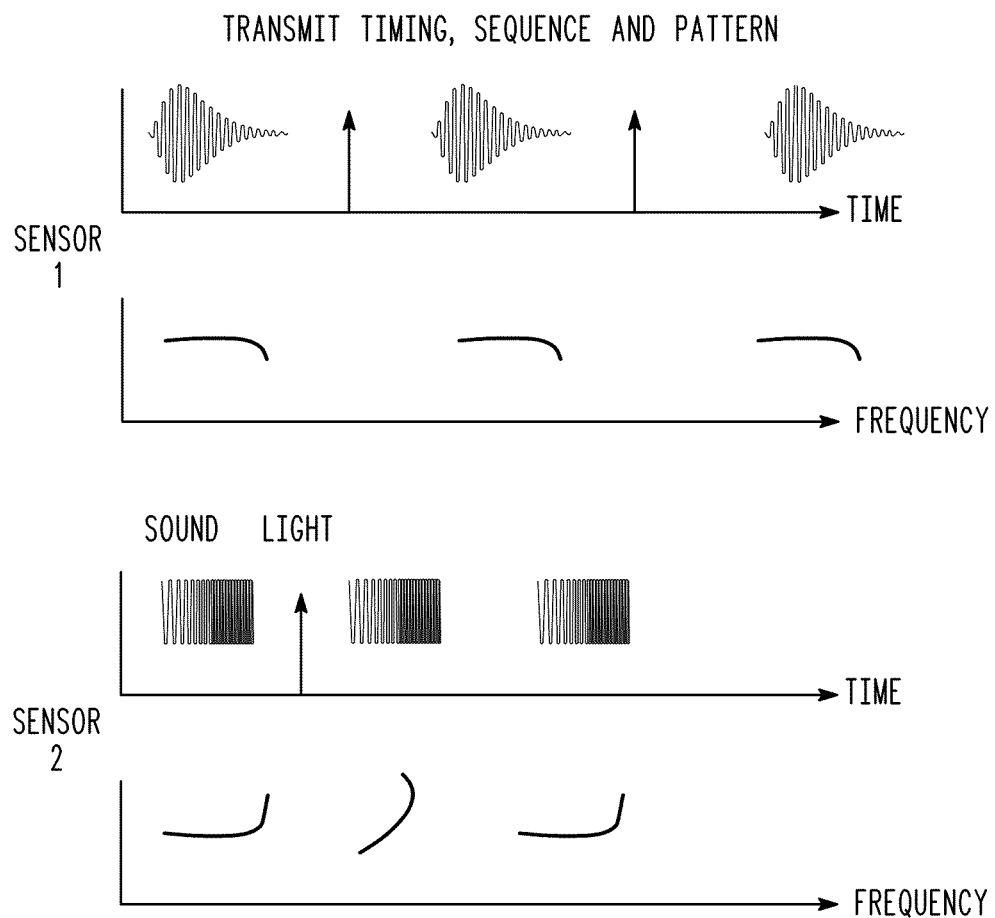
FIG. 1E depicts an exemplary sensory timing diagram in accordance with one embodiment.

FIG. 1E depicts an exemplary diagram for local communication and point registration between the wand 102 and the sensor 101. It illustrates transmit timing, sequence and pattern information using a combination of ultrasonic and optical signal processing according to one embodiment. The wand 102 simultaneously transmits a light signal (e.g., infrared pulse) with the ultrasonic pulse to signify sequence start of each ultrasonic pulse. The light signal is received at the sensor 101 to trigger timing of the received sound signal (e.g., ultrasonic pulse). The sensor 101 determines the time of flight of the ultrasonic pulse responsive to receiving the light signal, including any compensatory time information. For instance, a clock counts the elapsed time or is sequenced to an oscillator circuit.

The transmit characteristics of the ultrasonic pulse can change as a function of time, frequency and intensity as shown in FIG. 1E. One example of an ultrasonic transducer for pulsing is presented in U.S. Pat. No. 7,414,705 entitled "Method and System for Range Measurement", the entire contents of which are hereby incorporated by reference. The pulse duration, harmonic frequency content, frequency profile characteristics, phase and amplitude can all be adaptively changed during alignment measurement to maximize signal to noise ratio, distance measurement, and environmental conditions (e.g., temperature, drift, etc.). As one example, the microphone can assess noise floors and convey this information to a processor to adjust the ultrasonic pulse characteristics. As one example, each transmit sensor on the wand 102 can individually adjust it's transmit amplitude and frequency to mitigate interference and/or generate selective interference patterns. The sensor 101 can process the interference patterns via pattern detection, look up tables, spectral distortion measures, or statistical signal processing approaches to refine position estimates (e.g., <x,y,z> location). One example of an ultrasonic sensor is disclosed in U.S. Pat. No. 7,725,288 the entire contents of which are hereby incorporated by reference. The ultrasonic sensors can transmit pulse shaped waveforms in accordance with physical characteristics of a customized transducer for constructing and shaping waveforms Another embodiment incorporates synchronized clocks on both the wand 102 and sensor 101. A light pulse can initiate or reset synchronization. The synchronization is timed with the ultrasonic travel time and estimated wand 102 locations. As yet another example, Radio Frequency (RF) pulsing can be used to trigger onset timing of an ultrasonic pulse. The RF pulse can be transmitted with the ultrasonic pulse to identify the start time for measuring the ultrasonic pulse travel time. The sensor 101 and the wand 102 can be calibrated prior to use to ensure proper synchronization. In one configuration, bringing the wand 102 in close proximity to the sensor 101 can perform a calibration function, reset synchronization, or adjust another user function. One example of an ultrasonic sensing for such configuration is presented in U.S. patent application Ser. No. 11/562,404 entitled "Method and System for Object Control" filed Nov. 21, 2006, the entire contents of which are hereby incorporated by reference.

Figure 1F:
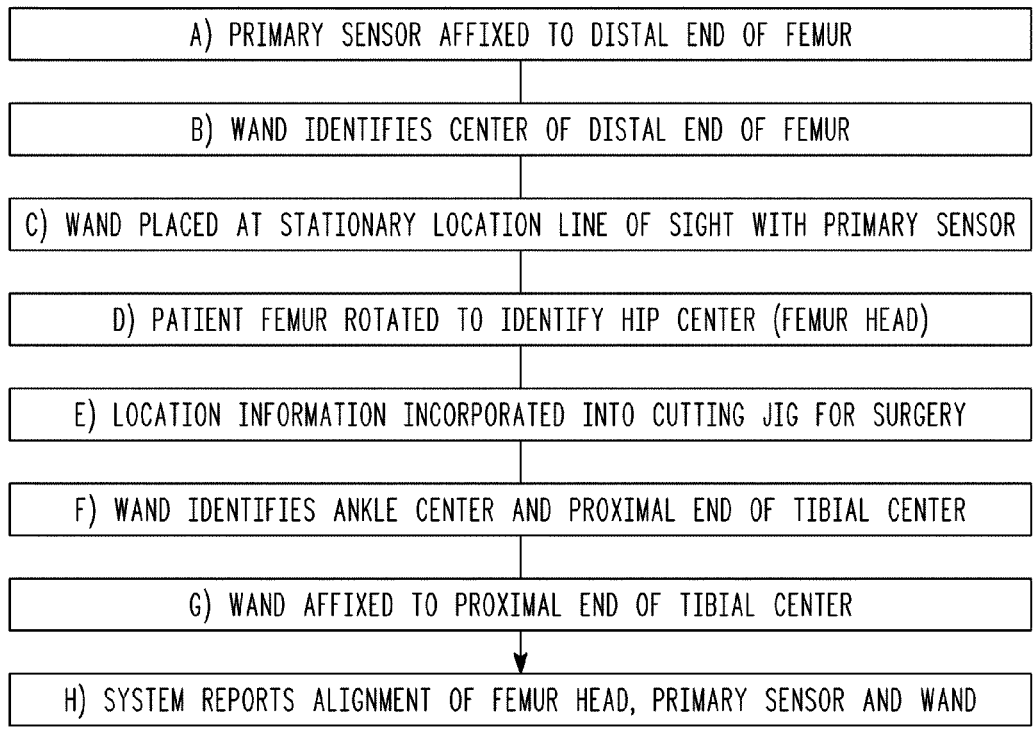
FIG. 1F is an exemplary method for assisted guidance navigation in accordance with one embodiment.

FIG. 1F depicts an exemplary method for assisted guidance navigation by way of the portable wireless alignment system 100. The method can be practiced with more or less than the number of steps shown and is not limited to the order shown. Completion of the method steps during surgical operation is on the order of 5-7 minutes.

The method can begin at step A in which the surgeon affixes the primary sensor 101 to the distal end of femur or a cutting jig 112 (see FIG. 1). As an example of affixing, a screw post 124 can include a detachable magnetic assembly to temporarily couple the sensor 101 to the bone or jig 112. At step B, the surgeon uses the wireless wand to identify the center of the distal end of femur. The surgeon touches the location(s) corresponding to the femur extension center and/or flexion center. The surgeon depresses a user interface component (e.g., touchpad, button, switch, etc.) on the wand 102 or speaks a voice command to register the point. The location information can be visually displayed on the communication device 104, for example, rendered in three-dimensions (3D) with the bone and/or cutting jig.

Upon affixing the primary sensor 101 and registering the femur center, the surgeon then places the wand at a stationary location with a line-of-sight to the primary sensor 101 at step C. As one example, the wand 102 is coupled to an extending base on an overhead operating light within the operating room. Placing the wand 102 above the operating space provides a clear signal path to other sensors or devices while being out of the surgical work area. At step D, the surgeon rotates the patient's femur for 10-15 seconds to identify the hip center (femur head). The sensor 101 processes the time of flight (TOF) and delta (dTOF) information to identify the 3D location of the stationary wand 102 with respect to the rotating (moving) sensor 101. It can further incorporate optical pattern information for example with navigation systems using infrared components. As one example, the processor within the sensor 101 can perform a least means square (LMS) operation from the spherical surface points to estimate a radius and center of the femur movement; to correspond to the femur head. A general likelihood test metric or adaptive filter can further resolve the femur head center. Receive data (e.g., acoustic waveform, zero crossings, peaks, etc.) can be buffered into memory and selectively indexed according to closest distance or distortion metrics. One example of a memory configuration is presented in U.S. patent application Ser. No. 12/146,445 entitled "Method and Device for Enhancing Accuracy in Ultrasonic Range Measurement" filed Jun. 26, 2008, the entire contents of which are hereby incorporated by reference.

The location information is incorporated into the cutting jig for surgery at step E. Computer Aided Topography (CAT) scans and Magnetic Image Resonance (MRI) scans can be further employed to resolve the femur head location in conjunction with the sensor 101 information. Three-dimensional (3D) CAT and MRI scans loaded into the communication device 104 for example prior to surgery during another registration process can be scanned in view of the sensor 101 information to confirm the femur head location. Registration can be performed to correlate the position of the wand in the surgical field and the corresponding location on the CT or MRI images. Femur neck geometries (e.g., angle, vector, magnitude) are also incorporated when projecting spherical best-fit techniques to the projected rotation data.

Figure 3:
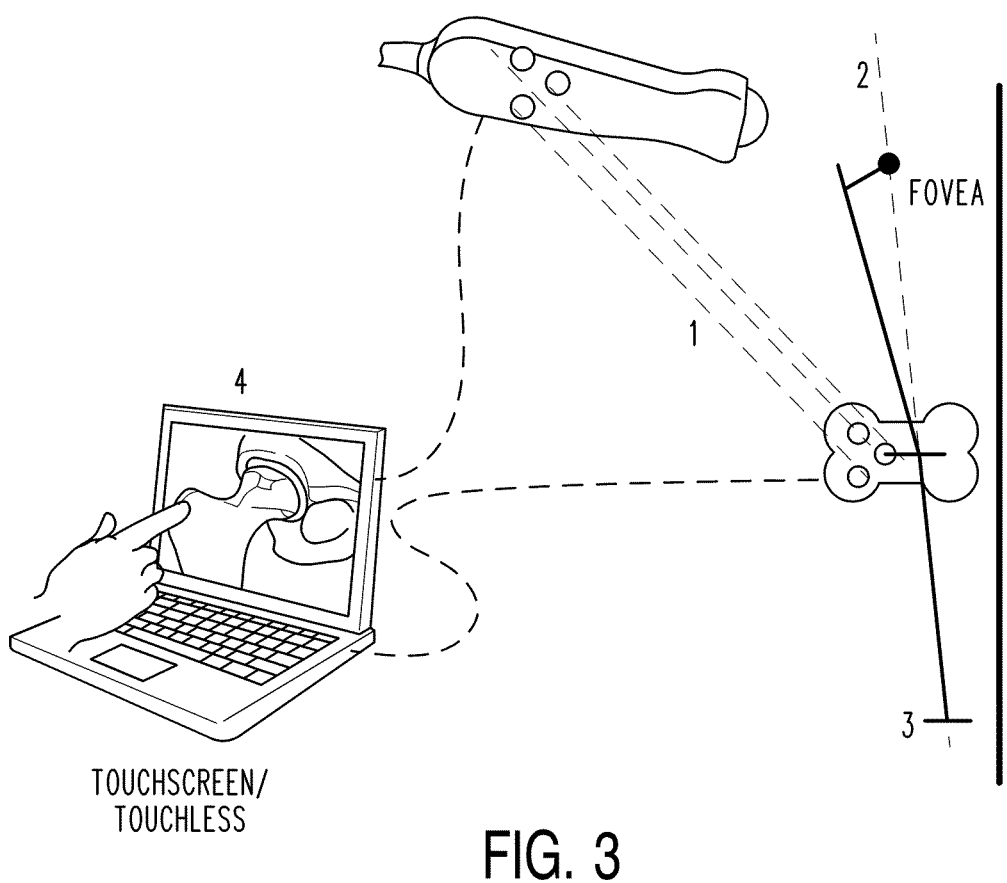
FIG. 3 depicts an exemplary diagram for identifying a femur head via hand-held ultrasound scanning in accordance with one embodiment.

As one example, FIG. 3 briefly depicts an exemplary embodiment where a portable hand-held ultrasound probe or scanner can be used to identify the femur head center. This process can be performed just prior to surgery during patient preparation for further femur head confirmation. The hand-held probe is operatively coupled to the communication device 104 to show the ultrasound scan. The surgeon can scan the hip area and then point via a touchless finger gesture or touch-screen to identify and register the femur head. The system 100 incorporates the visually identified femur head location with the spatial femur head position derived from the sensor 101 and wand 102 arrangement. One example of an ultrasonic control is presented in U.S. patent application Ser. No. 11/566,156 entitled "Method and System for Activating a Touchless Control", the entire contents of which are hereby incorporated by reference.

Returning back to the method of FIG. 1F, at step F, the surgeon uses the wand to identify the ankle center and thereafter the proximal end of tibia center. The left side of the ankle then the right side can be briefly taped to register the ankle contour. The sensor 101 can then estimate the ankle center through a weighted average (e.g., 0.6 distance factor). This registers the distal tibia point of interest (ankle center) with the sensor 101. The surgeon then at step G, affixes the wand 102 to the proximal end of tibia center or to a tibial cutting jig 112 (see FIG. 1). In this position the wand 102 is stationary and in direct communication with the sensor 101. The surgeon can then adjust the tibial cutting jig or the tibia to achieve proper alignment. The system 100 reports alignment of femur head, primary sensor and wand at step H.

Figure 1G:
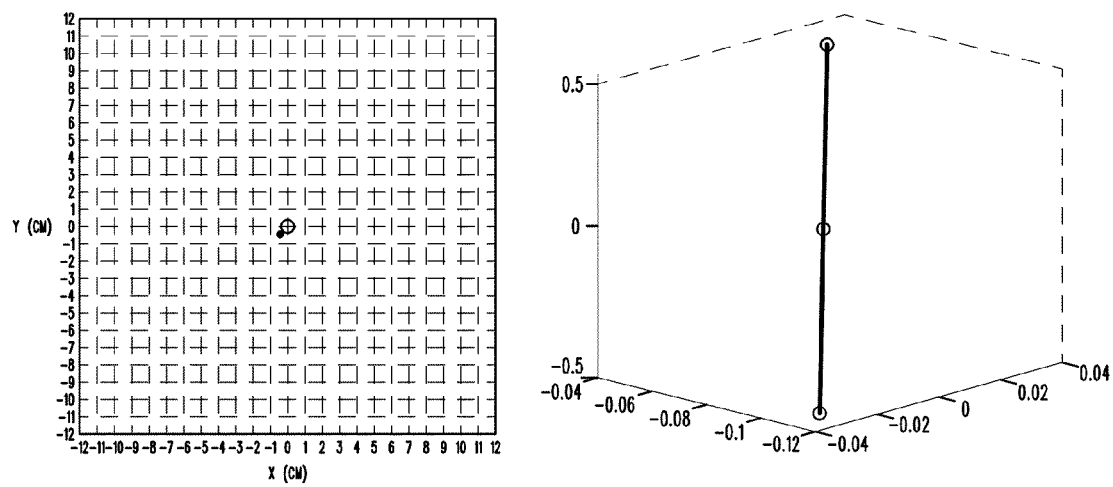
FIG. 1G depicts an exemplary display for assisted guidance navigation in accordance with one embodiment.

FIG. 1G shows a generic 3D Graphical User Interface (GUI) of alignment between three points representing the femur head, patella (knee cap) and ankle center. The points move in real time with the movement of the leg bones or attached jigs with sensors. Although shown on the display of the communication device 104, it can also be presented on the user interface of the sensor 101 itself, for example, via 3 or more LED lights. Alignment is achieved when the end points are overlaid with one another as in the left subplot and are in alignment as shown in the right subplot. Alignment precision is on the order of millimeters. In a general configuration, wand 102 is stationary and approximately 20" overhead the hip center, Sensor 101 is at the knee joint and approximately 18" from the hip center, and wand 102 when placed at the ankle center is approximately 19" from S2. The workflow takes about 5-7 minutes from start to generate alignment results.

The alignment tool supports 3D rendering in real-time. It shows multiple views and reports an alignment angle as the sensors are moved in physical space. It shows a i) main perspective view, ii) top view, and iii) side view. Mouse controls permits zoom, scaling and rotation on each separate view. The display can be further customized for user interface controls to render the views, communicate with the hardware, and other UI functionality. The alignment angle can be modified to report valgus and varus deviations.

Disclosed hereinbelow are low-level steps of an orthopedic operating room surgical workflow in accordance with an exemplary embodiment. In the example, reference to FIGS. 1A-1D, FIG. 4A, FIG. 7, and FIG. 8 will be made. The method can be practiced with more or less than the number of steps shown and is not limited to the order shown. In a first step, information and patient data is provided to a first GUI page for commencing the workflow. It can be input to the remote system 104, which in the present embodiment hosts the GUI 107. In one embodiment, GUI 107 hosts the customized workflow for the total knee replacement procedure. An example of a navigated workflow is disclosed in U.S. patent application Ser. No. 12/900,878, the entire contents of which are hereby incorporated by reference. The patient name and surgery information can be entered into the GUI 107. It also documents a time in and time out to confirm the patient with the procedure. A reader can also be coupled to system 104 for scanning information on the prosthetic components used prior to installation.

In a second step, the sterilized components (sensorized tools) of the navigation system 100 are opened, activated and calibrated. This includes: sensor 101, a mounted wand (not shown), and hand-held wand 102 (hereinafter system components). The calibration is a short procedure where the system components are validated for user requirement accuracy. In a third step, the system components broadcast their activation. The GUI 107 indicates (e.g., visual, auditory, and/or haptic) that the system components are on and operational according to specification.

After the patient is prepped for surgery the GUI 107 transitions to a femur registration page with information to provide visual guidance. The knee is opened with a longitudinal incision to expose the knee joint. Retractors are applied to protect soft tissue. In a fourth step, a femur pin can be placed in the distal femur. The sensor 101 is mounted to the femur pin (in or out of incision). As an example of affixing, a screw post can include a detachable magnetic assembly to temporarily couple the sensor 101 to the bone. Other affixing means are herein contemplated. The printed circuit board 126 is angled medially such that the sensor 101 is line-of-sight to the mounted wand.

In the example, the GUI 107 transitions to a tibia registration page. In a fifth step, a tibial pin can be pinned in the proximal tibia or midway on the tibia. The mounted wand is mounted to the tibial pin to be line-of-sight with the sensor 101. Similar mounting mechanisms can be included to ensure a rigid attachment of the mounted wand to the tibial pin.

In a sixth step, the wand 102 is temporarily mounted to a stationary stand and angled towards the sensor 101. The stationary stand can be affixed to a table, equipment, or overhead within the sterile field. Wand 102 serves as a reference location for the sensor 101 when the sensor 101 is moving, as will be disclosed ahead. The wand 102 can be placed within close proximity of the sensor 101, for example, within 2 meters, and out of the way of the mechanics of the procedure.

In a seventh step, the tibia is moved through a first range of motion (ROM1) from extension (straight leg) to flexion (knee bent ~90 degrees) to ensure the sensor 101 and the mounted wand remain sufficiently in line-of-sight; approximately −60 to 60 degrees face-to-face incident angles. The GUI 107 confirms local line of sight between the sensor 101 and the mounted wand during the step. The GUI 107 can provide sensory feedback to visually or audibly indicate line-of-site conditions, for example, turning red or green accordingly or specifying vocally that the components are line of sight.

In an eighth step, the GUI 107 transitions to a femoral Identification (ID) page. It instructs the surgeon to place the hip in flexion and apply gentle femoral rotation. The rotation is shown on the upper portion of the display in FIG. 7. This motion is applied in a ninth step to allow the sensor 101 to identify the femoral head (e.g., hip joint). One example of determining the femur head center is disclosed in U.S. patent application Ser. No. 12/900,955 filed Oct. 8, 2010 entitled "Orthopedic Method and System for Mapping an Anatomical Pivot Point, the entire contents of which are included by reference in entirety. Another is based on pivot point determination in U.S. Pat. No. 7,788,607, the entire contents of which are hereby incorporated by reference. The GUI 107 visually confirms this second range of motion (ROM) in the step, for example, by indicating a green status for line-of-sight in a tenth step. Typically, line of sight is approximately ±60 degrees conical to maintain user requirement precision, but can approach up to ±90 degrees for some applications. It indicates a red status when the ROM is outside the line-of-sight. In an eleventh step, GUI 107 informs the surgeon when the femoral head is registered and located within accuracy—it shows data collection, timestamp, and check points. The femur head establishes a first point for mechanical axis alignment of the leg.

Once the GUI 107 confirms femur head identification, the wand 102 is removed from the stationary (overhead) stand in a twelfth step. It is thereafter used to register the anatomical landmarks during the workflow procedure. In a thirteenth step, the GUI 107 instructs the surgeon to register distal femoral center with wand tip 134. The GUI 107 also indicates visually or audibly if the wand 102 falls out of the line-of-sight and/or requires surgeon to re-register landmarks. In the example, the locations of the lowest points on distal femoral condyles (medial and lateral), epicondyles, anterior cortex of distal femur, and posterior femoral condyles (PFC) (medial and lateral) are registered by wand 102.

In a fourteenth step, the GUI 107 instructs the surgeon to use the wand 102 to register the tibial landmarks such as the center of tibia (base of ACL) and the deepest points on proximal medial and lateral tibial plateau. In a fifteenth step, the GUI 107 instructs the surgeon to use the wand 102 to register landmarks of the ankle such as the medial malleolus and the lateral malleolus. During the registration disclosed above, the GUI 107 visually shows the registered points on the display in 3D, but is not limited to only the registration of these points. It also displays the desired mechanical axis of the leg for the leg in extension case (see FIG. 1, line ABC).

In a sixteenth step, dynamic knee data and leg information is captured related to the patient's current leg alignment and knee flexion. This information is recorded and reported. The knee flexion is specified by an angle indicating the amount of hyperextension through full bending of the knee (flexion). This angle can be between −10 to +120 degrees depending on the patient's condition. The GUI 107 instructs the surgeon to place the knee in extension and hold the leg steady to register the extension angle and mechanical axis. The knee is then moved through a full range of motion while the sensor 101 collects flexion data through minimum to maximum range. The GUI 107 tracks and reports the femur and tibia during the movement through the range of motion.

Figure 8:
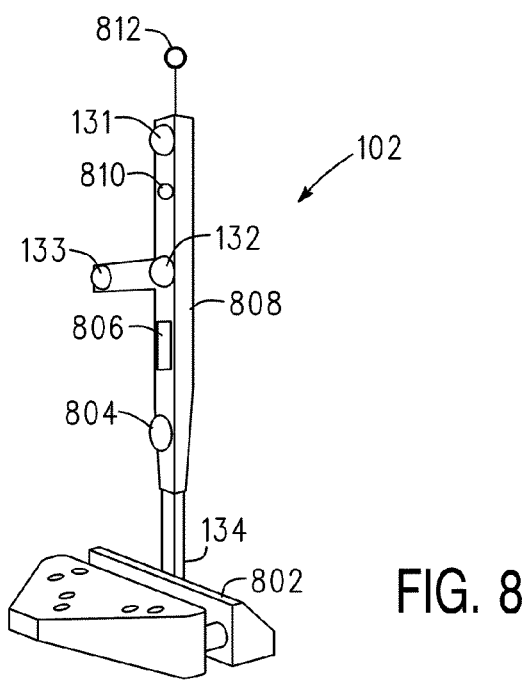
FIG. 8 is an illustration of the wand retained in a mount in accordance with an exemplary embodiment.

In a seventeenth step, the GUI 107 transitions to a femoral resection and instrumented cutting jig page. The knee is placed in flexion. During this step, the mounted wand may be temporarily removed from the tibial pin if it is in the way, but remounted in a later step ahead. The wand 102 is then mounted to a femoral cutting jig. Referring to FIG. 8, the wand 102 is shown in more detail. The illustration shows wand 102 coupled to a mount 802. In one embodiment, mount 802 is a cutting block or cutting jig. For example, mount 802 is a cutting block that couples to a distal end of the femur. Mount 802 is aligned by the alignment process to the femur for guiding a saw to generate bone cuts that have a relationship to the mechanical axis of the leg. This permits the sensor 101 to track translation and orientation of the cutting jig component (e.g. mount 802) for establishing femoral cutting angles specific to a prosthetic component in an eighteenth step. During navigation of the cutting jig, the GUI 107 displays the distal femur and registered femoral features, tracking of the femoral cutting jig, cutting planes with depth of cut to each registered distal condyles, flexion/extension angle of cutting plane relative to femoral mechanical axis, and varus-valgus angle of cutting plane relative to femoral mechanical axis. The mount 802 includes a feature for receiving and retaining tip 134 of wand 102. The feature can be a compression fit, threaded for coupling to tip 134, or magnetic to name but a few retaining methods contemplated. Similar approaches can be used for mount 802 attached in other locales within the surgical field to position wand 102 in fixed line of sight position. A feature 802 can be used to couple wand 102 to a light fixture, overhead, or to an attaching feature within the surgical field that is out of the way but in communication to the measurement system.

Wand 102 has a body 802 that allows a user to easily hold the device in the hand for registering points of interest. A control 804 is accessible to the hand or fingers for controlling operation of the device. In one embodiment, control 804 can be a switch or a scrolling device with switching capability. Control 804 can be used in conjunction with an interface 806 on the body 804 of wand 102. A transducer 810 can receive vocal or audible signals. The vocal signals are coupled to a digital signal processor of the measurement system having voice recognition software. Recognized terms or phrases are then converted into actions by a software program that can be performed by the measurement system. One example of voice recognition in a navigated workflow with the sensorized tools is disclosed in U.S. patent application Ser. No. 12/099,662 entitled "Method and Device for Virtual Navigation and Voice Processing" filed Apr. 8, 2008 and claiming priority to Provisional Patent Application 60/911,082 filed Apr. 11, 2007; the entire contents of which are hereby incorporated by reference. The wand 102, sensor 101, remote module 104 and the mounted wand can be responsive to the vocal commands. Furthermore, each active component of the system can have a transducer for receiving vocal commands and communication circuitry to wirelessly couple to the digital signal processor. Ultrasonic transducers 131-133 extend from the body 802 of wand 102. The extensions on wand 802 place ultrasonic transducers 131-133 the predetermined distance apart from each other to support three-dimensional location identification. Another example of voice recognition in a navigated workflow is disclosed in U.S. patent application Ser. No. 12/723,486 entitled "Sterile Networked Interface for Medical Systems" filed Mar. 12, 2010 and claiming priority to Provisional Patent Application 61/159,793 filed Mar. 12, 2009; the entire contents of which are hereby incorporated by reference.

In an nineteenth step, the femoral cutting jig is positioned and navigated in view of the GUI 107 and pinned securely to the distal femur for the desired cutting plane. The distal end of the femur is then cut. The femoral cutting jig is then unpinned and placed bottom flat surface on the cut distal femoral surface to verify cut accuracy; that is, it is laid against the cut. The GUI 107 reports distal femoral cut accuracy based on the positioning of the wand 102 mounted to the cutting jig.

Figure 4A:
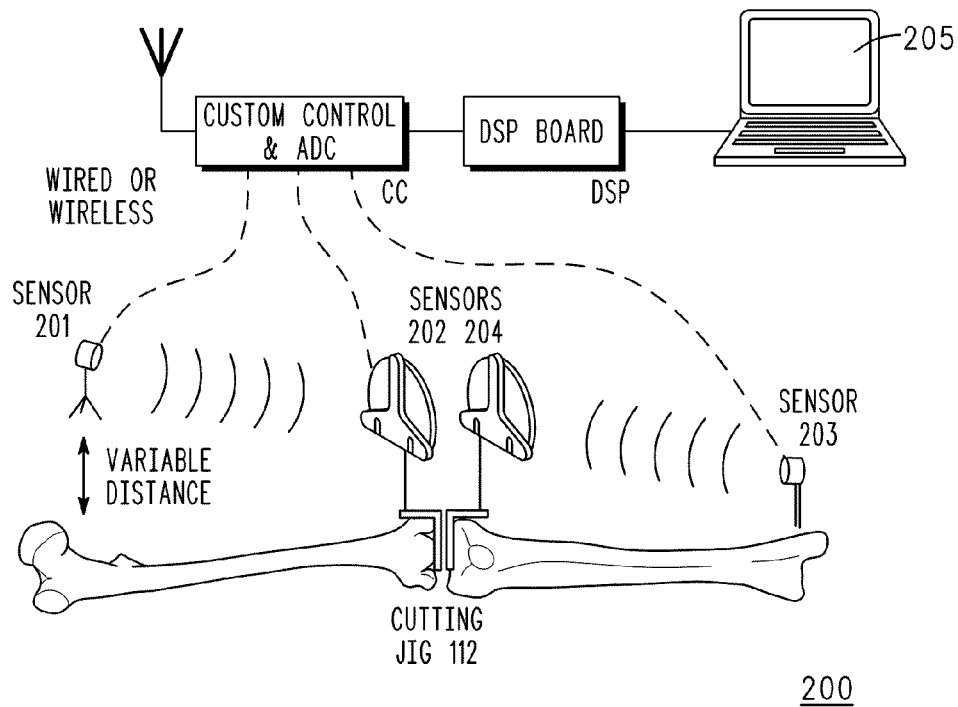
FIG. 4A depicts a disposable device for assisted alignment in accordance with one embodiment.

The GUI 107 then transitions to the tibial resection and instrumented cutting jig page. The wand 102 is then removed from the femoral cutting jig and attached to a tibial cutting jig in a twentieth step. Referring to FIG. 4A, additional sensors can be provided to make the process more efficient. Sensor 204 can be attached to the tibial cutting jig for locating a point in three-dimensional space. Sensor 203 can be an additional wand used to register points. As shown and disclosed herein additional sensors can be used during the knee procedure if desired. Referring back to FIG. 1A, during this time, the mounted wand may be remounted to the tibial pin if it was previously removed. In a twenty-first step, the repositioning of wand 102 permits the sensor 101 to track translation and orientation of the tibial cutting jig for establishing tibial cutting angles to make tibial cuts. In one embodiment, the GUI 107 displays tibia and registered tibial features, the tibial cutting jig, the cutting plane with depth of cut to lowest points on medial and lateral tibial plateau, varus-valgus angle of cutting plane relative to the tibial mechanical axis, and anterior/posterior slope relative to the tibial mechanical axis.

In a twenty-second step, the tibial cutting jig is positioned and navigated in view of the GUI 107 and pinned securely to the tibia for the desired cutting plane. The proximal end of the tibia is then cut. Bony or meniscal remnants are removed from the cut area. The tibial cutting jig is then unpinned and placed bottom flat surface on the cut proximal tibial surface to verify cut accuracy. The GUI 107 reports proximal tibial cut accuracy based on the positioning of the wand 102 mounted on the tibial cutting jig.

In a twenty-third step, upon completion of the tibial cut, the knee is extended with an extension block to assess extension gap and confirm gap resection. The extension gap is a volumetric void between the distal femur end and the proximal tibia end; a portion of the void was created due to the cutting of the femur bone end and the tibial bone end, which had partially occupied that region prior to cutting. The GUI 107 displays the measured gap distances and varus/valgus alignment in a twenty-fourth step. These measurements can be verified by the navigation system in addition to the extension block. The gap distance is a function of knee flexion and indicates the flexibility and strength of the medial and lateral knee tendons. The gap distance in extension (leg straight) can differ from the gap distance in flexion (leg bent) by a few millimeters. It also provides an indication of a permitted level of soft tissue release for achieving proper balance and alignment, which is performed in a twenty-eighth step. The gap distance is also assessed in order to determine appropriate chamfer cutting angles on the distal femur and proximal tibia and trial insert sizes.

The GUI 107 then transitions to a femoral Anterior-Posterior (AP) and chamfer cuts page. The knee is placed in flexion. In a twenty-sixth step, the wand 102 is mounted to a 4-in-1 cutting block, which is a sophisticated jig that provides four different cutting angles in one block. The AP position and rotary position of the 4-in-1 cutting block is then defined in view of the GUI 107. The GUI 107 shows the location and orientation of the (sensorized) 4-in-1 block relative to the cutting planes and registered anatomical features. In a twenty-seventh step, the 4-in-1 block is positioned and navigated in view of the GUI 107 and pinned securely for the desired cutting plane. The AP cut is made and thereafter the chamfer cuts are made on the distal femur end in the twenty-eighth step. Upon making the first series of cuts, a tensioning device is then applied off the tibia in a twenty-ninth step to distract the knee joint to cause the ligaments to rotate the femur until it is parallel to the cut tibial plateau (ligament tensioning technique). The 4-in-1 block is then positioned and navigated in view of the GUI 107 with the incorporated AP positioning. The 4-in-1 block is pinned securely for the desired cutting plane and the final AP and chamfer cuts in a thirtieth step.

Figure 9:
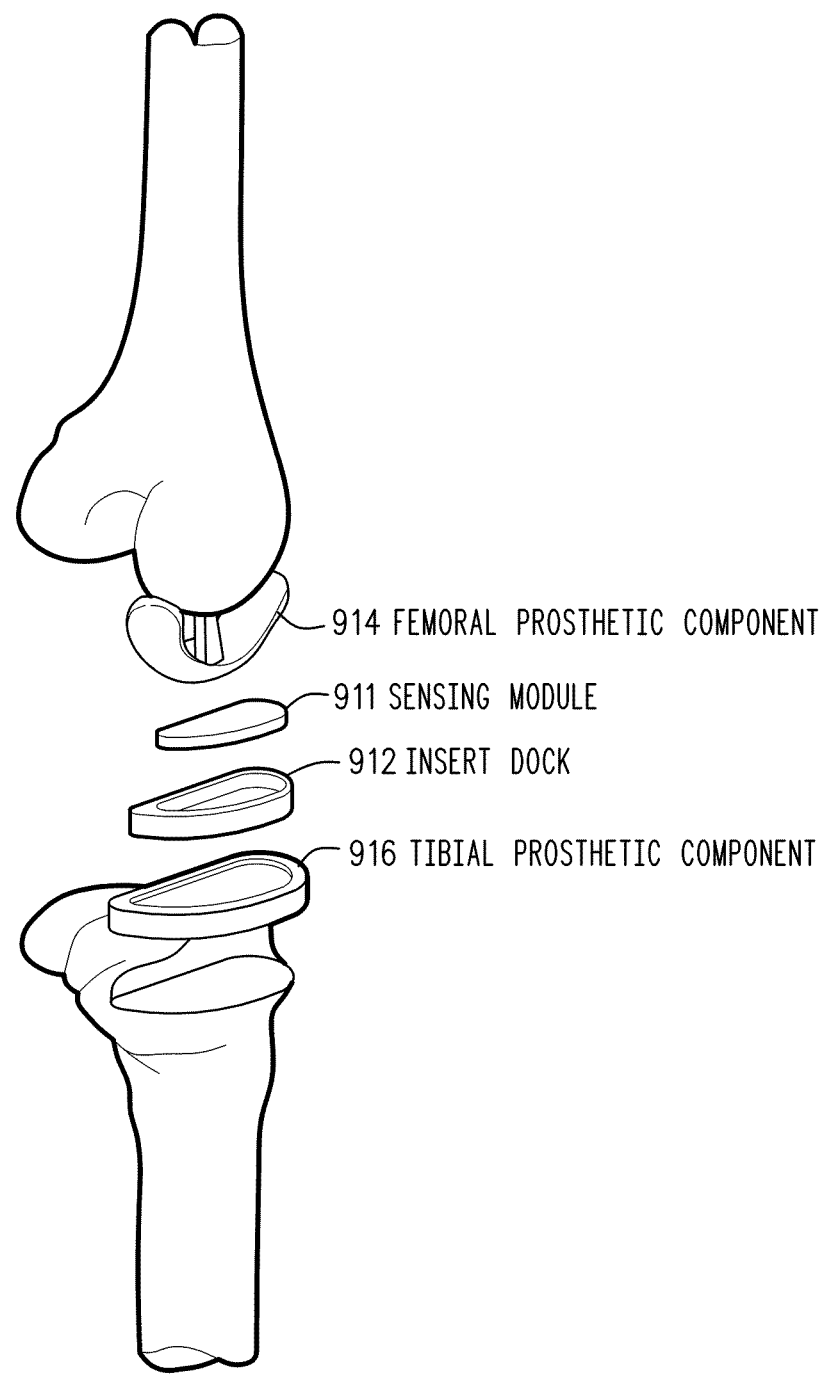
FIG. 9 is an illustration of knee prosthetic components in accordance with an exemplary embodiment.

The GUI 107 then transitions to an insert trialing page, which guides the surgeon through selecting trial inserts. In a thirty-first step, the femoral and tibial implant trials with tibial insert trial are inserted. During this procedure, a load sensing insert device can also be embedded within the tibial trial insert to assess balance. Thus, multiple parameters of the muscular-skeletal system are being measured providing the surgeon with quantitative data to support subjective feel during surgery. An exemplary relationship is illustrated among such components that comprise a prosthetic knee implant: the sensing module 911, the femoral prosthetic component 914, tibial prosthetic (tray or plate) component 916, and the tibial insert dock 912 in FIG. 9. The load sensing insert device 911 provides a concave articular surface against which the outer condylar articulating surface of the femoral prosthetic component 914 rides relative to the tibia prosthetic component 916. Examples of a load sensing insert sensing module are described in ORTHO-01US, U.S. patent application Ser. No. 12/825,638 entitled "SYSTEM AND METHOD FOR ORTHOPEDIC LOAD SENSING INSERT DEVICE", ORTHO-07US, U.S. patent application Ser. No. 12/825,724 entitled "WIRELESS SENSING MODULE FOR SENSING A PARAMETER OF THE MUSCULAR-SKELETAL SYSTEM", ORTHO-10US, U.S. patent application Ser. No. 12/825,770 entitled "INTEGRATED SENSOR FOR MEDICAL APPLICATIONS", ORTHO-27US, U.S. patent application Ser. No. 12/826,329 entitled "SENSING MODULE FOR ORTHOPEDIC LOAD SENSING INSERT DEVICE" all filed Jun. 29, 2010; the entire contents of each which are hereby incorporated by reference herein. In such a configuration, the navigation system 100 reports combined balance and alignment information by way of the GUI 107.

Referring back to the operative steps of the knee example, the knee is removed through a third range of motion to assess implant stability, slipping and proper fit in a thirty-second step. During the third range of motion, the GUI 107 displays the knee with extension angle and mechanical axis in a thirty-third step. It also displays combined balance and alignment information when the sensing module 911 is included therein. The GUI 107 reports knee flexion, balance and alignment while the knee is moved through maximal flexion through extension to hyperextension as permitted. During the third range of motion, the knee may be subluxed posteriorally in flexion in view of the GUI 107 to define any posterior instability. In a thirty-fourth step, the patella is cut and trialed. The femur bone and tibia are then prepped for implant and cemented in a thirty-fifth step and the final poly is inserted. The knee is moved through a final range of motion in view of the GUI 107 displaying the extension angle and mechanical axis to validate balance and alignment in a thirty-sixth step.

Figure 2A:
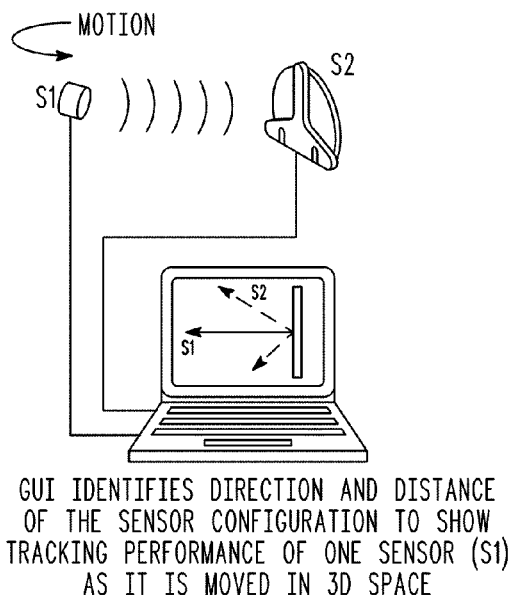
FIG. 2A depicts an exemplary Graphical User Interface for tracking a sensor in accordance with one embodiment.
Figure 2A:
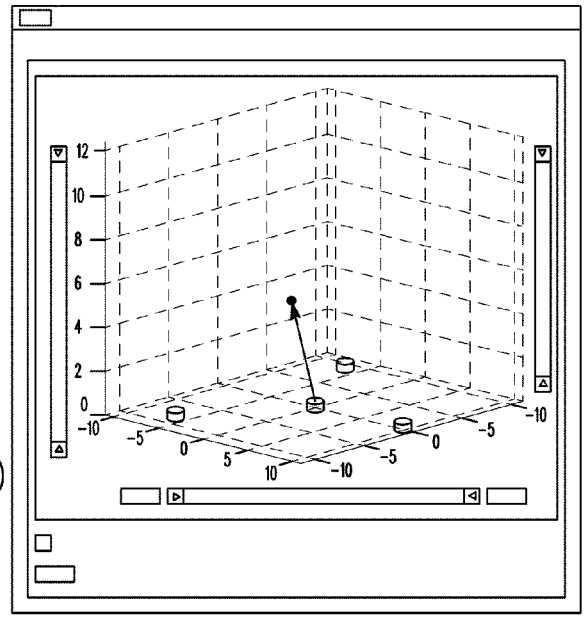

FIG. 2A depicts an exemplary GUI that visually identifies a direction and distance of the sensor configuration to show tracking performance of one sensor as it is moved in 3D space as in step B.

Figure 2B:
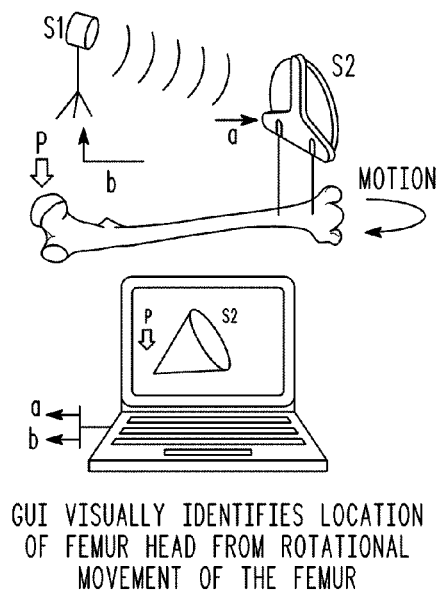
FIG. 2B depicts an exemplary Graphical User Interface for identifying a femur head from rotational movement in accordance with one embodiment.
Figure 2B:
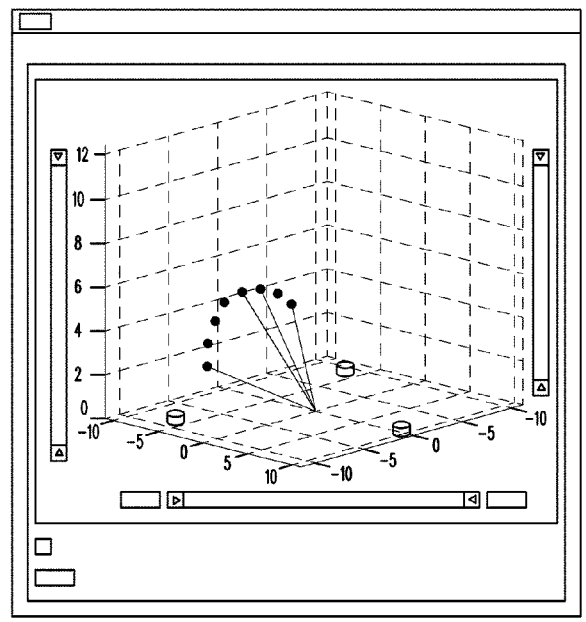

FIG. 2B depicts an exemplary GUI that visually identifies a location of the femur head from rotational movement of the femur as in step D.

Figure 2C:
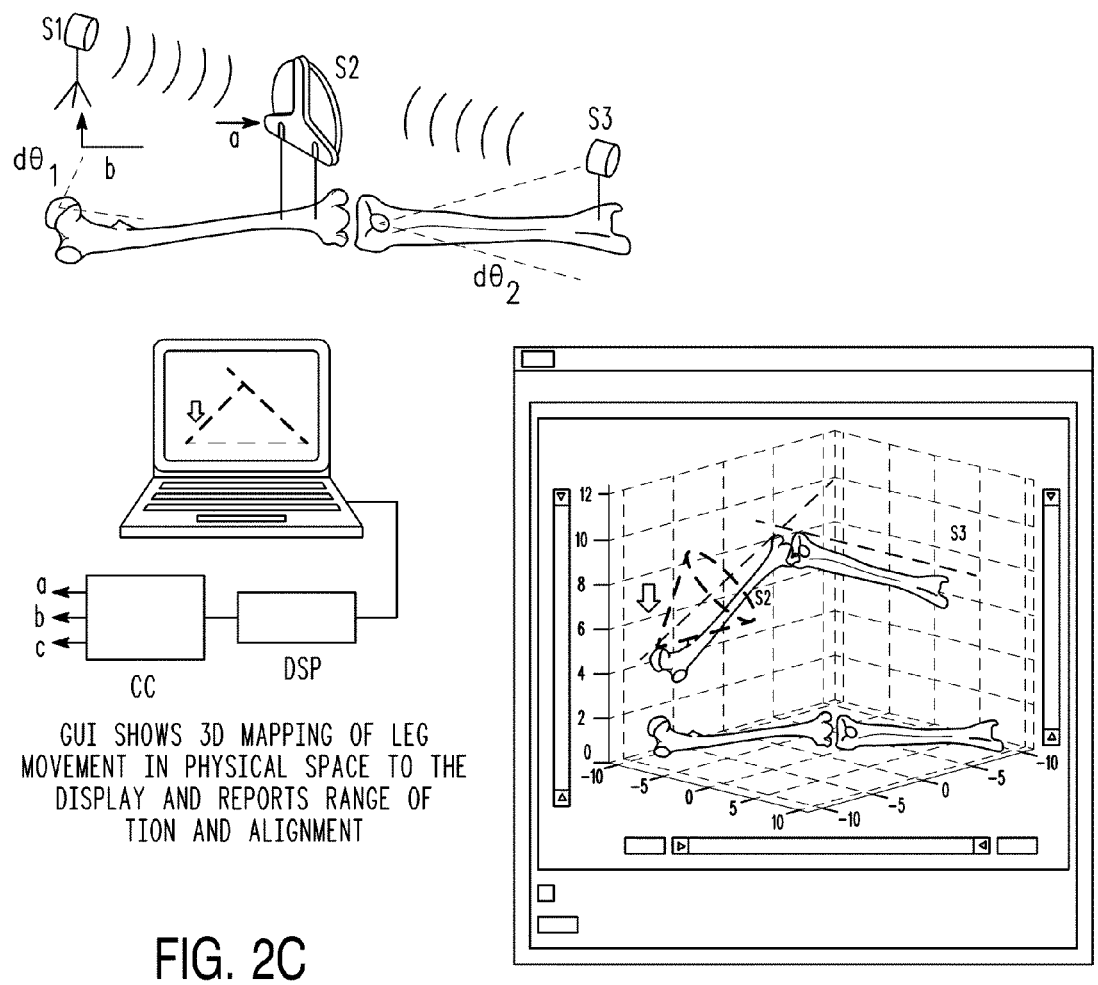
FIG. 2C depicts an exemplary Graphical User Interface for mapping and reporting leg movement in accordance with one embodiment.

FIG. 2C depicts an exemplary GUI that visually shows mapping of leg movement in physical space to the display and reports range of motion and alignment as in step H.

Figure 2D:
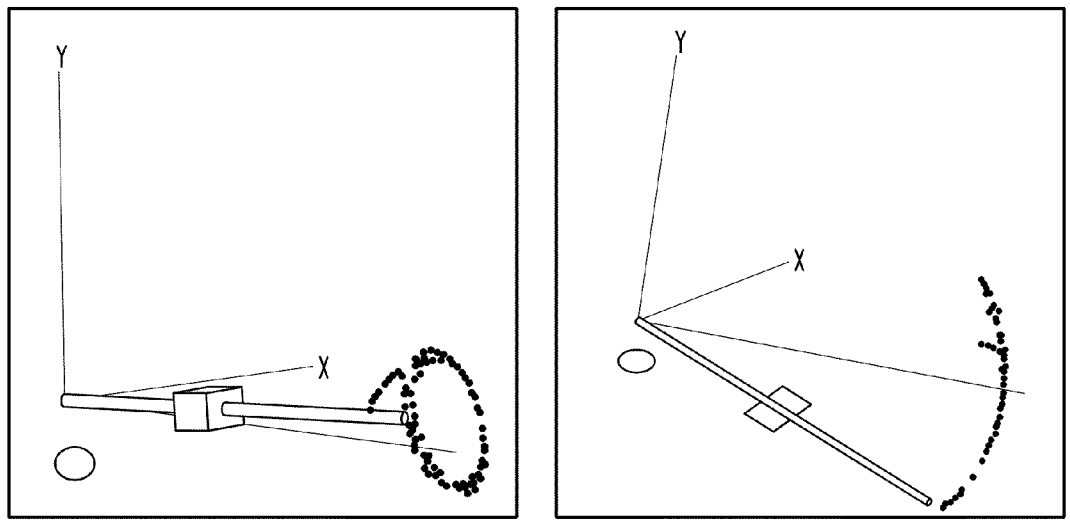
FIG. 2D depicts an exemplary Three-Dimensional (3D) User Interface for spherical centroid identification of a femur head in accordance with one embodiment.

FIG. 2D shows a three-dimensional (3D) software Graphical User Interface (GUI) display. The alignment tool plots the positional location (green dots) of the TX relative to the RX (<0,0,0> origin of white stick) during real-time movement of the femur. The physical configuration produces a 3D loci of points on a spherical surface that is used to identify the centroid (e.g., pivot point; yellow dot). Five hundred (500) surface points or less can be used to calculate the centroid (10 seconds of moving the femur).

Figure 2E:
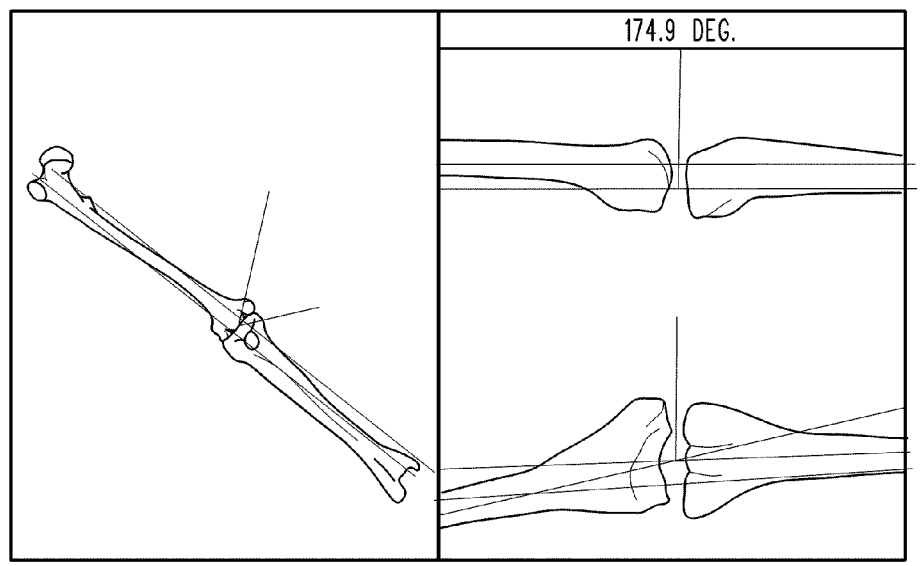
FIG. 2E depicts an exemplary Three-Dimensional (3D) User Interface for orthopedic alignment in accordance with one embodiment.

FIG. 2E shows a three-dimensional (3D) software Graphical User Interface (GUI) display. Yellow line shows femoral axis; purple line shows tibial axis; and green line shows femoral head center point with ankle center point. Alignment is achieved at 180° (or 0° valgus/varus) when green line overlays purple line in top and side views. Perspective view permits viewing of femur and tibia center. The displayed bones move in 3D virtual space as the femur and tibia are moved in physical space.

FIG. 4A depicts another exemplary embodiment of a portable assisted guidance system 200 similar in function to the sensor-wand configuration of FIG. 1A. The system 200 comprises a group of sensors 201-204 communicatively coupled to an acquisition system 205 by way of a wired or wireless connection. The group of sensors 201-204 can be individually hermetically sealed for clean room conditions during surgery. The acquisition system 205 can comprise a custom control board (CC) a DSP board and a laptop, although, in other embodiments, the CC and DSP can operate internally from a customized laptop using electronic processing resources therein (e.g., processor, memory, converters, etc.)

The system 200 is portable in that it can be managed by the laptop and the sensors 201-204, which are self-contained and disposable. As one example, each sensor 201-204 can be individually packaged prior to surgery and specific to the surgical procedure performed. Each sensor can include one or more ultrasonic transducers that in addition to being used for alignment can provide an embedded bar code. The acquisition system 205 by way of each individual and labeled sensor can perform automatic data logging and asset tracking prior to and during surgery; information, which can be, relayed to a database administration system or healthcare records.

Each sensor 201-204 can be entirely sealed in a disposable plastic package. An adhesive can affix it to the patient prior to surgery. A sensor can also comprise one or more sensing elements (e.g., MEMS ultrasonic transducer, optical element, laser, camera) for permitting three-dimensional tracking, for example by way, of sound localization, optical line of sight, optical pattern recognition, or any combination thereof. The sensor can include other processing components in addition to just the sensing elements (e.g., acoustic transducers, optical elements, infra-red elements, etc.).

Figure 4B:
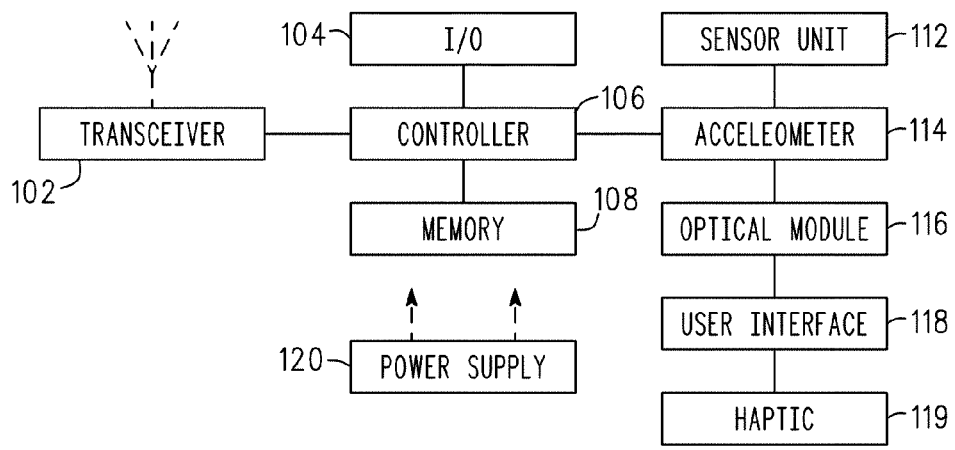
FIG. 4B depicts a block diagram of components of the disposable alignment device in accordance with one embodiment.

FIG. 4B depicts a block diagram of an exemplary sensor 201-204 suitable for use in the portable assisted guidance system 200 of FIG. 4A. With respect to FIG. 4A, each sensor 201-204 in the system 200 may contain more or less than the number of components shown depending on function. For instance, Sensor 201 and Sensor 203 may contain only an ultrasonic sensor with a transceiver for strictly disposable use. Sensors 202 and 204 may contain all the components shown in FIG. 4B. The sensor can be waterproof and shock absorbent.

In a wireless communications setting, the transceiver 102 can utilize common technologies to support singly or in combination any number of wireless access technologies including without limitation, FM modulation (FSK, PSK, GPSK, BSK, etc.), Bluetooth™ 802.15, Wireless Fidelity (Wi-Fi) 802.11a/b/g/n, Worldwide Internet access 802.16 (WiMAX), Ultra Wide Band (UWB), software defined radio (SDR), and cellular access technologies such as CDMA-1X, W-CDMA/HSDPA, GSM/GPRS, TDMA/EDGE, and EVDO. SDR can be utilized for accessing a public or private communication spectrum according to any number of communication protocols that can be dynamically downloaded over-the-air to the terminal device. It should be noted also that next generation wireless access technologies can be applied to the present disclosure.

The controller 106 can utilize computing technologies such as a microprocessor (µP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. The Input/Output 104 permits portable exchange of information or data for example by way of Universal Serial Bus (USB). The electronic circuitry of the controller 106 can comprise one or more Application Specific Integrated Circuit (ASIC) chips, for example, specific to a core signal processing algorithm. The controller 206 can be an embedded platform running an operating system (OS), such as windows mobile or Android. In one arrangement, the storage memory may store one or more sets of instructions (e.g., software) embodying any one or more of the methodologies or functions described herein.

The sensor unit 112 can comprise ultrasonic sensors, MEMS sensors, microphones or any combination thereof. As one example, the sensor unit 112 can comprise both narrowband and broadband ultrasound source and receivers (40 to 200 KHz) capable of localization of received signals by triangulation through time of flight (TOF) and differential TOF (dTOF) measurements; at least 3 broadband ultrasound receivers and 1 broadband directed source with spread of approximately 120 degree conical section can be used.

The accelerometer 114 measures the acceleration it experiences relative to gravity or motion. Single- and multi-axis MEMS models detect magnitude and direction of the acceleration as a vector quantity, and can be used to sense orientation, vibration and shock. By way of the accelerometer 114 sensor 130 can determine orientation or movement relative to one another.

The optical module 116 can detect and transmit visible light and infrared light. It can also record images as either a still photo or moving images. The optical module 116 can include optical sensors, light sensors, CCD, CMOS or MEMS elements to capture the light of the visible spectrum or use with other portions of the electromagnetic spectrum. The captured light data can be saved to internal memory or communicated there from by way of the transceiver 102.

The User Interface 118 can include one or more visual elements, such as a LED to indicate operation (e.g., green, yellow, red), or one or more interactive elements, such as a softkey or touchpad to initiate a process (e.g., on, off).

The Haptic module 119 can include a motor and a mechanical integrity device (accelerometer) for shock and vibration.

The power supply 120 can utilize common power management technologies such as replaceable batteries, supply regulation technologies, and charging system technologies for supplying energy to the components of the terminal device and to facilitate portable applications. The power supply can include ultra-capacitors for energy storage. In clinical settings, the power supply 214 can be modified to extract energy from a common wall outlet for charging to supply DC power to the components of the terminal device 106. The charging can also be performed by inductive means while the sensor device remains in sanitary packaging.

Drive and receive electronics can be contained on a PCB inside the sensor and contain analog interface circuitry, A/D and D/A circuits and DSP or microprocessor. Power can be delivered via wireless magnetic induction or USB cable to main processor module. The sensor can include a super capacitor for smooth energy delivery and filtering of transients from burst operation.

The processor can include a unique hardware key for registering use of the device and for medical reporting. To ensure single use, the system can connect to a server for registration to receive encrypted key. The service center can send a program with the embedded key to ensure proper medical use. The key information can be hidden and retrieved by authorized persons. The sensors 101 can deactivate after such use or after a pre-specified amount of time.

Figure 4C:
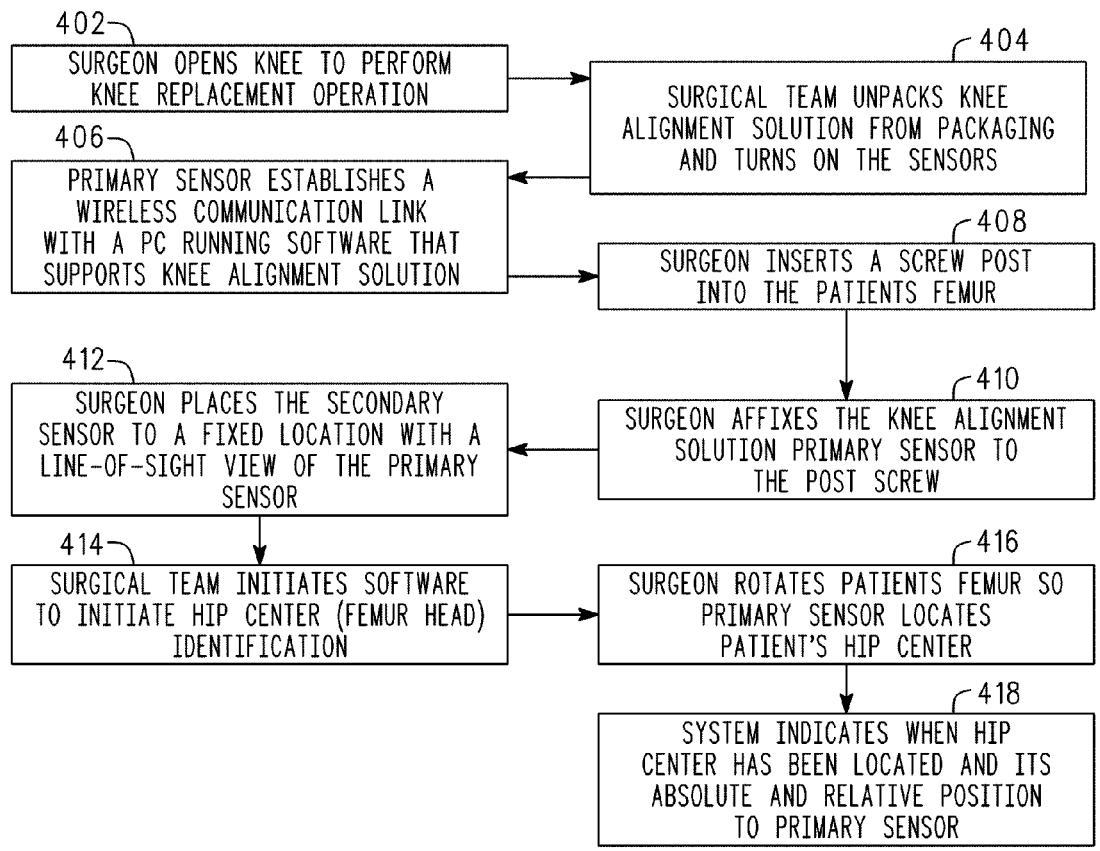
FIG. 4C is an exemplary method for assisted guidance navigation in accordance with one embodiment.

FIG. 4C depicts an exemplary method for femur head identification by way of the system 200. The method can be practiced with more or less than the number of steps shown and is not limited to the order shown.

The method can begin at step 402 in which Surgeon opens knee to perform knee replacement operation. At step 404, the surgical team unpacks the knee alignment solution from packaging and turns on the sensors. At step 406, the primary sensor establishes a wireless communication link with a PC running software that supports knee alignment solution. The Surgeon inserts a screw post into the patient's femur and allows a connector portion of the post to remain accessible at step 408. The Surgeon then at step 410 affixes the knee alignment solution primary sensor to the connector. The primary sensor and connector can have a narrow profile on the order of less than 2×6×8 inches (W,L,H). The tall and slim profile keeps the electronics and sensor housing up vertically away from the lateral, medial, anterior and posterior surgical areas. At step 412, the Surgeon places the secondary sensor to a fixed location with a line-of-sight view of the primary sensor. At step 414, the surgical team initiates software to initiate hip center (femur head) identification.

Figure 5A:
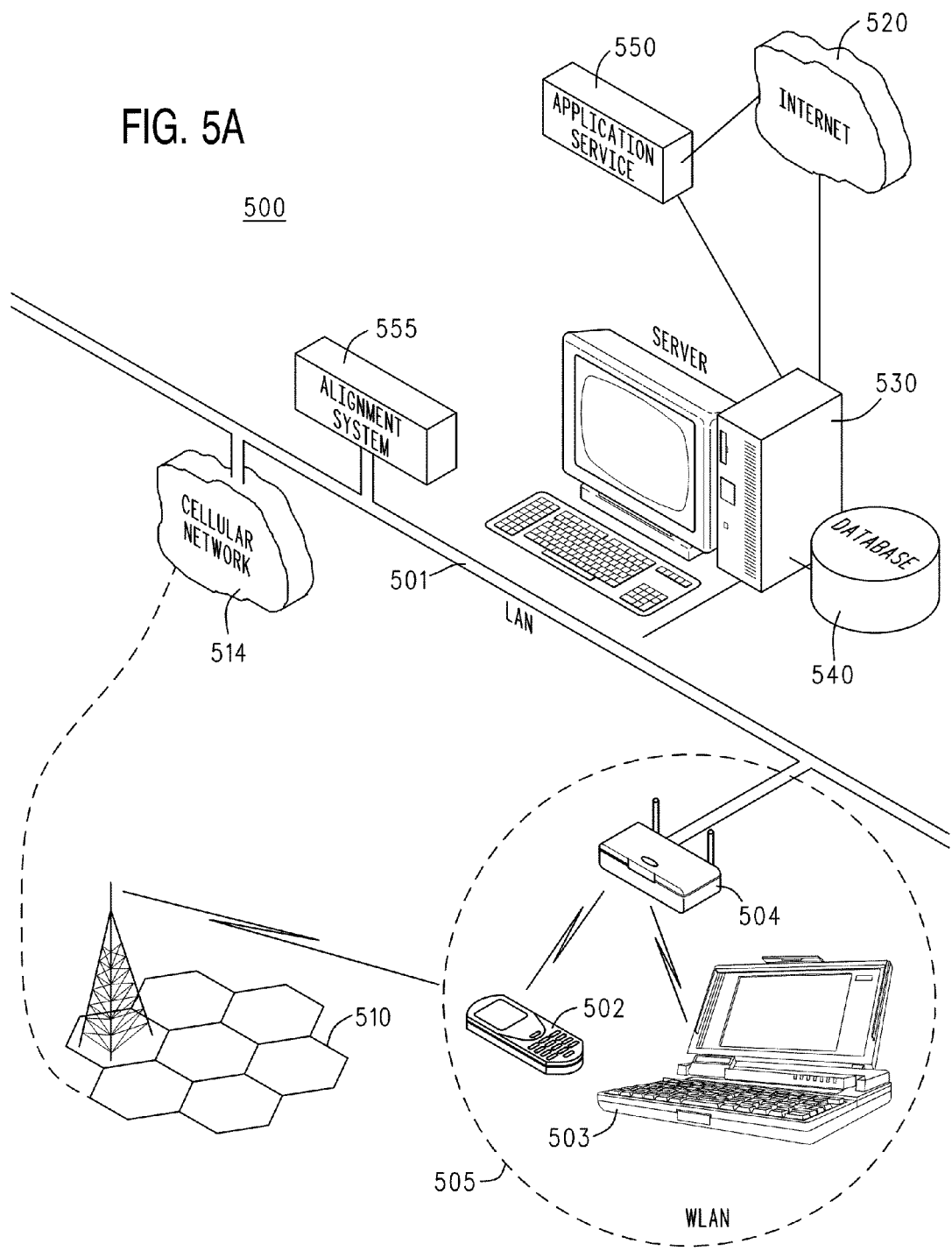
FIG. 5A depicts an exemplary communication system for one of several embodiments of the alignment system in accordance with one embodiment.

The Surgeon rotates patients femur at step 416 so primary sensor locates patient's hip center. At step 418, the system indicates when a hip center has been located and its absolute and relative position to the primary sensor. Referring to FIG. 5A, a communication network 500 for alignment detection and reporting is shown. Briefly, the communication network 500 expands broad data connectivity to other devices or services. As illustrated, the alignment detection and reporting system 555 can be communicatively coupled to the communications network 500 and any associated systems or services.

As one example, the alignment system 555 can share its parameters of interest (e.g., angles, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 500 can further be tied to an Electronic Medical Records (EMR) system to implement health information technology practices. In other embodiments, the communication network 500 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 500 can provide wired or wireless connectivity over a Local Area Network (LAN) 501, a Wireless Local Area Network (WLAN) 505, a Cellular Network 514, and/or other radio frequency (RF) system (see FIG. 4). The LAN 501 and WLAN 505 can be communicatively coupled to the Internet 520, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 500 can utilize common computing and communications technologies to support circuit-switched and/or packet-switched communications. Each of the standards for Internet 520 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 514 can support voice and data services over a number of access technologies such as GSM-GPRS, EDGE, CDMA, UMTS, WiMAX, 2G, 3G, WAP, software defined radio (SDR), and other known technologies. The cellular network 514 can be coupled to base receiver 510 under a frequency-reuse plan for communicating with mobile devices 502.

The base receiver 510, in turn, can connect the mobile device 502 to the Internet 520 over a packet switched link. The internet 520 can support application services and service layers for distributing data from the load sensing system 555 to the mobile device 502. The mobile device 502 can also connect to other communication devices through the Internet 520 using a wireless communication channel.

The mobile device 502 can also connect to the Internet 520 over the WLAN 505. Wireless Local Access Networks (WLANs) provide wireless access within a local geographical area. WLANs are typically composed of a cluster of Access Points (APs) 504 also known as base stations. The load sensing system 555 can communicate with other WLAN stations such as laptop 503 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc).

By way of the communication network 500, the alignment system 555 can establish connections with a remote server 530 on the network and with other mobile devices for exchanging data. The remote server 530 can have access to a database 540 that is stored locally or remotely and which can contain application specific data. The remote server 530 can also host application services directly, or over the internet 520.

Figure 5B:
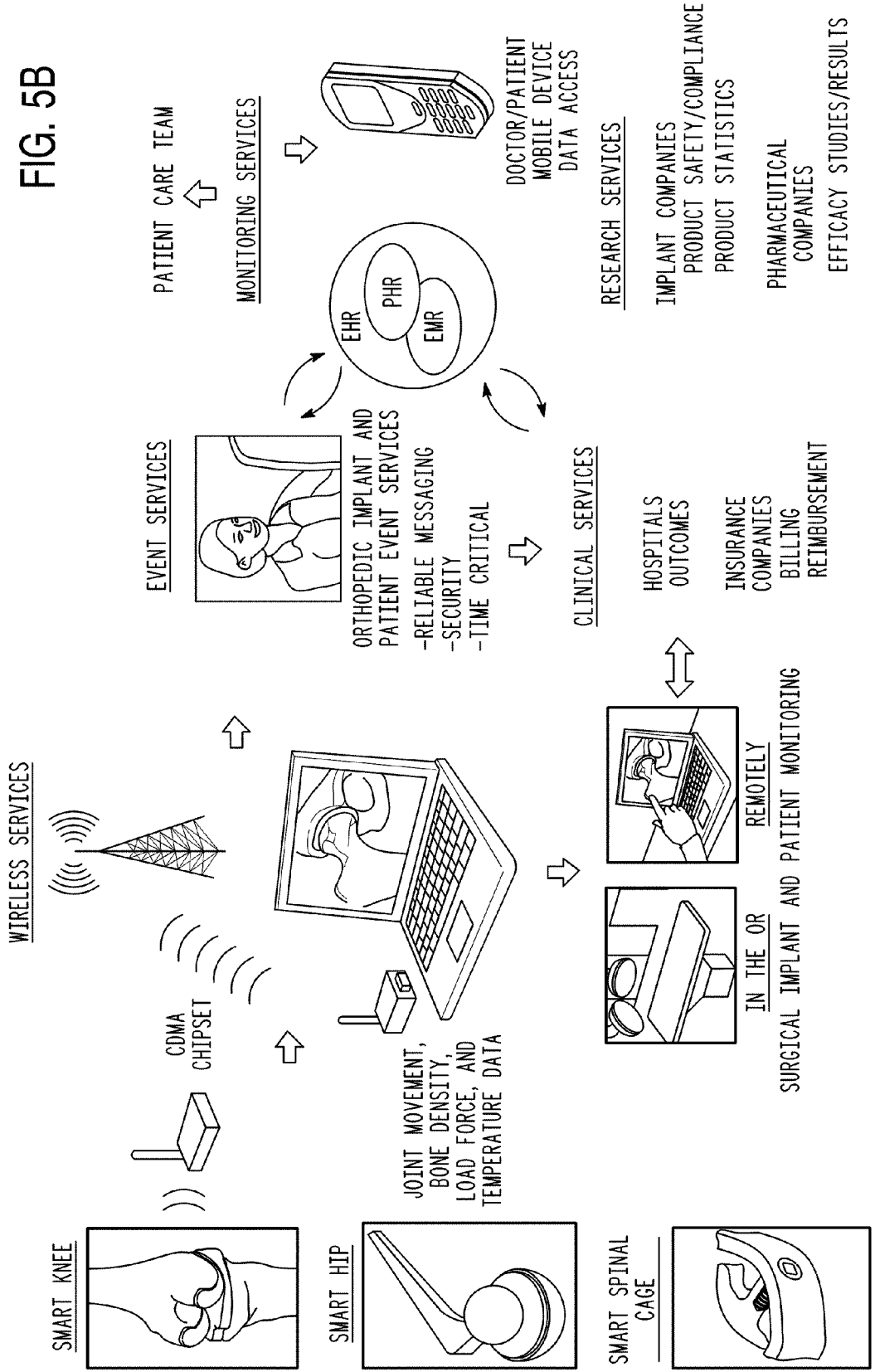
FIG. 5B depicts an exemplary diagram for event services and monitoring of smart orthopedic implants in accordance with one embodiment.

FIG. 5B shows one embodiment of the communication network 500 for managing smart implant products, services and applications. A smart implant for example can identify alignment, joint movement, bone density, load forces and temperature data. This information can be conveyed via wireless services, for example, over a telecommunication network to event service providers. The event services can include orthopedic implant and patient event services for time critical, secure, and reliable messaging and reporting. This information is related to monitoring services responsible for medical reporting, patient/doctor and consulting offices, and research services, including medical device and pharmaceutical companies.

Figure 6:
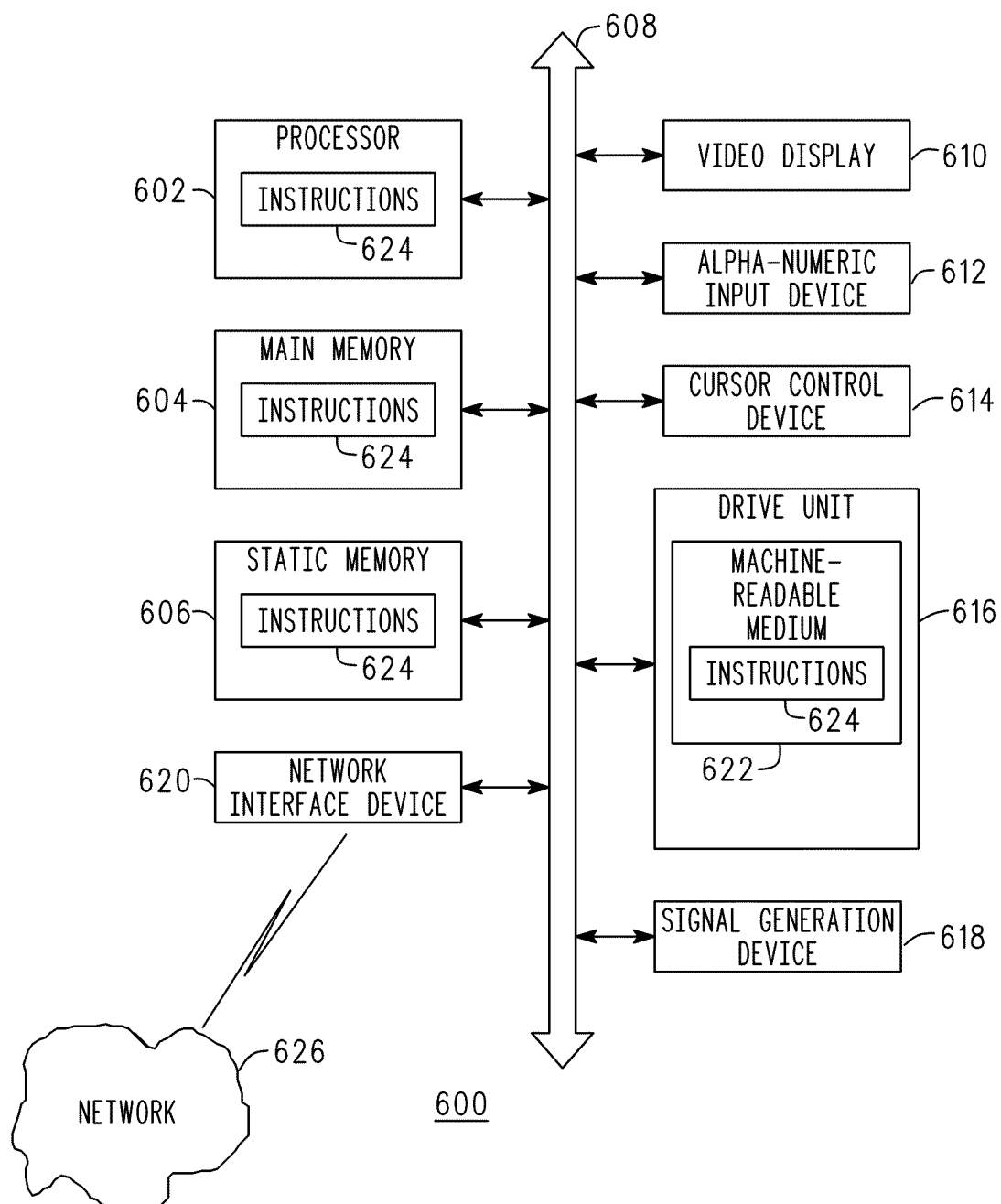
FIG. 6 depicts an exemplary diagrammatic representation of a machine in the form of a computer system within which a set of instructions, when executed, may cause the machine to perform any one or more of the methodologies disclosed herein.
Figure 7:
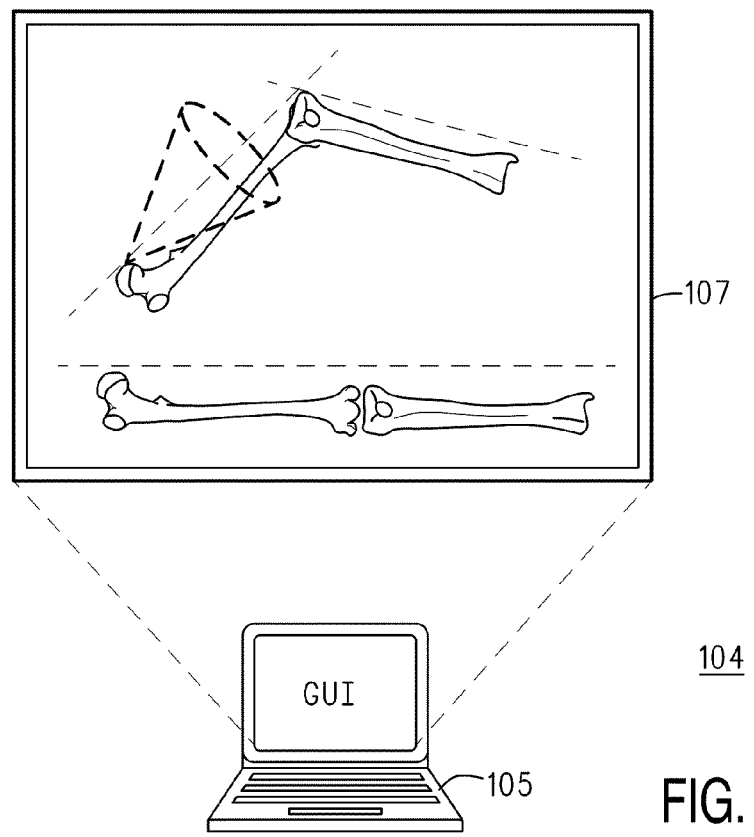
FIG. 7 is an illustration of a portable communication device having a GUI displaying alignment data in accordance with an exemplary embodiment.

FIG. 6 depicts an exemplary diagrammatic representation of a machine in the form of a computer system 600 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 600 may include a processor 602 (e.g., a central processing unit (CPU), a graphics processing unit (GPU, or both), a main memory 604 and a static memory 606, which communicate with each other via a bus 608. The computer system 600 may further include a video display unit 610 (e.g., a liquid crystal display (LCD), a flat panel, a solid state display, or a cathode ray tube (CRT)). The computer system 600 may include an input device 612 (e.g., a keyboard), a cursor control device 614 (e.g., a mouse), a disk drive unit 616, a signal generation device 618 (e.g., a speaker or remote control) and a network interface device 620.

The disk drive unit 616 may include a machine-readable medium 622 on which is stored one or more sets of instructions (e.g., software 624) embodying any one or more of the methodologies or functions described herein, including those methods illustrated above. The instructions 624 may also reside, completely or at least partially, within the main memory 604, the static memory 606, and/or within the processor 602 during execution thereof by the computer system 600. The main memory 604 and the processor 602 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 624, or that which receives and executes instructions 624 from a propagated signal so that a device connected to a network environment 626 can send or receive voice, video or data, and to communicate over the network 626 using the instructions 624. The instructions 624 may further be transmitted or received over a network 626 via the network interface device 620.

While the machine-readable medium 622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

What is claimed is:

1. A sensor for a surgical orthopedic alignment system comprising:
    at least two ultrasonic transducers located at predetermined positions relative to each other on the sensor;
    an accelerometer configured to identify axial tilt; and
    a controller operatively coupled to the at least two ultrasonic transducers and the accelerometer, where at least one of the at least two ultrasonic transducers are configured to measure ultrasonic signals, where the measured ultrasonic signals are used to calculate a time of flight, where the time of flight and a differential time of flight is used to calculate a location of an object in three-dimensional space within a surgical field, where the sensor is configured to be attached to a portion of the object, where the object is a portion of a muscular skeletal system, where the location of the object can be used by a processor to determine alignment of the muscular skeletal system and where a trigger system is configured to initiate a measurement process where a trigger signal is faster than an ultrasonic signal.

2. The sensor of claim 1 where the sensor further includes a mounting structure to attach the sensor in a reference position and where the mounting structure is configured to attach to bone, cutting block, or jig.

3. The sensor of claim 1 further including an infrared detector for receiving a trigger signal.

4. The sensor of claim 1 where the sensor further includes:
a printed circuit board and where the at least two ultrasonic transducers are coupled to a first side of the printed circuit board where each of the at least two ultrasonic transducers have a predetermined location on the printed circuit board for receiving signals directed thereto.

5. The sensor of claim 4 where a second side of the printed circuit board includes at least three ultrasonic transducers each at a predetermined location on the second side of the printed circuit board for receiving signals directed thereto.

6. The sensor of claim 1 further including an optical detector for receiving an optical trigger signal.

7. The sensor of claim 1 further including:
a power source coupled for powering the sensor; and
wireless communication circuitry coupled to the controller for transmitting alignment information.

8. The sensor of claim 1 wherein the sensor is line of sight with at least one wand.

9. The sensor of claim 1 where the sensor includes a user interface coupled to the controller that can visually or audibly report a status.

10. A wand for a surgical orthopedic alignment system comprising:
at least two ultrasonic transducers located at predetermined positions relative to each other on the wand;
a trigger system configured to initiate a measurement process and where a trigger signal is faster than an ultrasonic signal;
an accelerometer configured to identify axial tilt; and
a controller operatively coupled to the at least two ultrasonic transducers and the accelerometer, where at least one of the at least two ultrasonic transducers emits ultrasonic signals, where the emitted ultrasonic signals are measured and used to calculate a time of flight and a differential time of flight, where the time of flight and a differential time of flight is used to calculate a location of an object in three-dimensional space within a surgical field, and where the wand is configured to be line of sight to the sensor.

11. The wand of claim 10 further including:
a housing operatively formed for being handheld; and
a tip extending from the housing for registering one or more locations.

12. The wand of claim 11 where the tip is a touch sensitive tip that is responsive to a physical action.

13. The wand of claim 10 further including an optical emitter to send the trigger signal.

14. The wand of claim 10 further including an infrared emitter to send the trigger signal.

15. The wand of claim 10 further including:
a power source internal to the wand coupled for powering the wand;
a user interface coupled to the controller that can visually or audibly report a status; and
wireless communication circuitry coupled to a processor for transmitting information.

16. The wand of claim 10 further including an attachment mechanism to mount the wand to a bone, a cutting block, or a jig.

17. A surgical orthopedic alignment system comprising:
a wand having at least two ultrasonic transducers to transmit signals corresponding to a location of a muscular skeletal system in three-dimensional space where the wand includes an accelerometer configured to measure axial tilt;
a sensor having at least two ultrasonic transducers located at predetermined positions relative to each other to receive signals from the wand, where the surgical orthopedic alignment system is configured to measure a time of flight and a differential time flight of ultrasonic signals sent from the wand to the sensor, where the wand is line of sight to the sensor, where the sensor includes an accelerometer configured to measure axial tilt, and where the sensor is configured to be attached to a portion of the muscular skeletal system;
a trigger system coupled to the wand and the sensor configured to initiate a measurement process where a trigger signal is faster than the ultrasonic signals; and
a mount to retain and hold the wand in a second predetermined location where the wand, sensor, and mount are within a surgical field.

18. The alignment system of claim 17 where the trigger system comprises an optical emitter and an optical detector.

19. The alignment system of claim 17 where the trigger system comprises an infrared emitter and an infrared detector.

* * * * *